(12) United States Patent
Stearns et al.

(10) Patent No.: US 8,909,326 B2
(45) Date of Patent: *Dec. 9, 2014

(54) METHOD AND APPARATUS FOR 3-D IMAGING OF INTERNAL LIGHT SOURCES

(75) Inventors: Daniel G. Stearns, Mountain View, CA (US); Bradley W. Rice, Danville, CA (US); Michael D. Cable, Danville, CA (US)

(73) Assignee: Xenogen Corporation, Alameda, CA (US)

( * ) Notice: Subject to any disclaimer, the term of this patent is extended or adjusted under 35 U.S.C. 154(b) by 410 days.

This patent is subject to a terminal disclaimer.

(21) Appl. No.: 12/947,794

(22) Filed: Nov. 16, 2010

(65) Prior Publication Data

US 2011/0090316 A1  Apr. 21, 2011

Related U.S. Application Data

(63) Continuation of application No. 12/569,842, filed on Sep. 29, 2009, now Pat. No. 7,860,549, which is a continuation of application No. 10/606,976, filed on Jun. 25, 2003, now Pat. No. 7,616,985.

(60) Provisional application No. 60/395,357, filed on Jul. 16, 2002, provisional application No. 60/396,458, filed on Jul. 16, 2002, provisional application No. 60/396,313, filed on Jul. 16, 2002.

(51) Int. Cl.

| H04N 13/02 | (2006.01) |
|---|---|
| G01B 11/24 | (2006.01) |
| G01N 21/76 | (2006.01) |
| A61K 49/00 | (2006.01) |
| G01N 21/64 | (2006.01) |
| G01B 11/25 | (2006.01) |
| G01B 9/02 | (2006.01) |

(52) U.S. Cl.
CPC .......... *G01N 21/763* (2013.01); *A61K 49/0013* (2013.01); *G01N 21/6456* (2013.01); *G01B 11/24* (2013.01); *G01B 11/2518* (2013.01); *G01B 9/02004* (2013.01); *G01B 9/02041* (2013.01); *G01B 9/0203* (2013.01); *H04N 13/0271* (2013.01); *H04N 13/0203* (2013.01); *H04N 13/025* (2013.01)
USPC ...... 600/473; 348/46; 348/E13.074; 356/601; 600/407; 600/425; 600/476

(58) Field of Classification Search
CPC ............... G01B 11/24; G01B 11/2518; G01B 9/02004; G01B 9/02041; G01B 9/0203; H04N 13/0271; H04N 13/0203; H04N 13/025
USPC ............ 600/407, 476, 473, 425; 356/60–608; 382/128
See application file for complete search history.

(56) References Cited

U.S. PATENT DOCUMENTS

| 4,687,325 A | 8/1987 | Corby, Jr. |
| 4,687,352 A | 8/1987 | Igi et al. |

(Continued)

OTHER PUBLICATIONS

Final Office Action dated Nov. 15, 2010 from U.S. Appl. No. 11/844,551.

*Primary Examiner* — Vani Gupta
(74) *Attorney, Agent, or Firm* — Fish & Richardson P.C.

(57) ABSTRACT

The present invention provides systems and methods for obtaining a three-dimensional (3D) representation of one or more light sources inside a sample, such as a mammal. Mammalian tissue is a turbid medium, meaning that photons are both absorbed and scattered as they propagate through tissue. In the case where scattering is large compared with absorption, such as red to near-infrared light passing through tissue, the transport of light within the sample is described by diffusion theory. Using imaging data and computer-implemented photon diffusion models, embodiments of the present invention produce a 3D representation of the light sources inside a sample, such as a 3D location, size, and brightness of such light sources.

25 Claims, 14 Drawing Sheets

(56) References Cited

U.S. PATENT DOCUMENTS

| | | |
|---|---|---|
| 4,761,071 A | 8/1988 | Baron |
| 4,773,097 A | 9/1988 | Suzaki et al. |
| 5,202,091 A | 4/1993 | Lisenbee |
| 5,205,291 A | 4/1993 | Potter |
| 5,242,441 A | 9/1993 | Avitall |
| 5,319,209 A | 6/1994 | Miyakawa et al. |
| 5,334,193 A | 8/1994 | Nardella |
| 5,414,258 A | 5/1995 | Liang |
| 5,452,723 A | 9/1995 | Wu et al. |
| 5,584,872 A | 12/1996 | LaFontaine et al. |
| 5,594,253 A | 1/1997 | Bueno et al. |
| 5,636,299 A | 6/1997 | Bueno et al. |
| 5,637,874 A | 6/1997 | Honzawa et al. |
| 5,650,135 A | 7/1997 | Contag et al. |
| 5,661,562 A | 8/1997 | Aharon |
| 5,672,881 A | 9/1997 | Striepeke et al. |
| 5,705,807 A | 1/1998 | Throngnumchai |
| 5,738,101 A | 4/1998 | Sappey |
| 5,746,210 A | 5/1998 | Benaron et al. |
| 5,807,262 A | 9/1998 | Papaioannou et al. |
| 5,812,310 A | 9/1998 | Stewart et al. |
| 5,818,587 A | 10/1998 | Devaraj et al. |
| 5,835,617 A | 11/1998 | Ohta et al. |
| 5,840,572 A | 11/1998 | Copeland |
| 5,865,754 A * | 2/1999 | Sevick-Muraca et al. .... 600/476 |
| 5,867,250 A | 2/1999 | Baron |
| 5,917,190 A | 6/1999 | Yodh et al. |
| 5,943,129 A | 8/1999 | Hoyt et al. |
| 5,953,446 A | 9/1999 | Opsal et al. |
| 5,963,658 A | 10/1999 | Klibanov et al. |
| 5,970,164 A | 10/1999 | Bamberger |
| 5,983,121 A | 11/1999 | Tsuchiya |
| 6,069,698 A | 5/2000 | Ozawa et al. |
| 6,108,576 A | 8/2000 | Alfano et al. |
| 6,175,407 B1 | 1/2001 | Sartor |
| 6,205,347 B1 | 3/2001 | Morgan et al. |
| 6,205,353 B1 * | 3/2001 | Alfano et al. ................. 600/476 |
| 6,208,886 B1 | 3/2001 | Alfano et al. |
| 6,217,847 B1 | 4/2001 | Contag et al. |
| 6,219,566 B1 | 4/2001 | Weersink et al. |
| 6,230,046 B1 | 5/2001 | Crane et al. |
| 6,242,743 B1 | 6/2001 | DeVito et al. |
| 6,252,623 B1 | 6/2001 | Lu et al. |
| 6,264,610 B1 | 7/2001 | Zhu |
| 6,267,477 B1 | 7/2001 | Karpol et al. |
| 6,321,111 B1 | 11/2001 | Perelman et al. |
| 6,332,087 B1 | 12/2001 | Svenson et al. |
| 6,364,829 B1 | 4/2002 | Fulghum |
| 6,373,557 B1 | 4/2002 | Mengel et al. |
| 6,373,568 B1 | 4/2002 | Miller et al. |
| 6,377,353 B1 | 4/2002 | Ellis |
| 6,381,302 B1 | 4/2002 | Berestov |
| 6,392,241 B1 | 5/2002 | Rushbrooke et al. |
| 6,394,965 B1 | 5/2002 | Klein |
| 6,403,947 B1 | 6/2002 | Hoyt et al. |
| 6,415,051 B1 | 7/2002 | Callari et al. |
| 6,429,943 B1 | 8/2002 | Opsal et al. |
| 6,529,627 B1 | 3/2003 | Callari et al. |
| 6,549,288 B1 | 4/2003 | Migdal et al. |
| 6,597,931 B1 | 7/2003 | Cheng et al. |
| 6,615,061 B1 | 9/2003 | Khalil et al. |
| 6,615,063 B1 * | 9/2003 | Ntziachristos et al. ....... 600/312 |
| 6,618,152 B2 | 9/2003 | Toida |
| 6,618,463 B1 | 9/2003 | Schotland et al. |
| 6,628,401 B2 | 9/2003 | Toida |
| 6,628,747 B1 | 9/2003 | Schotland et al. |
| 6,636,755 B2 | 10/2003 | Toida |
| 6,642,953 B1 | 11/2003 | Nieto Velasco et al. |
| 6,646,678 B1 | 11/2003 | Kobayashi |
| 6,649,143 B1 * | 11/2003 | Contag et al. .................. 424/9.1 |
| 6,665,072 B2 | 12/2003 | Hoyt |
| 6,690,466 B2 | 2/2004 | Miller et al. |
| 6,690,520 B1 | 2/2004 | Kusuzawa |
| 6,693,710 B1 | 2/2004 | Hoyt |
| 6,710,770 B2 | 3/2004 | Tomasi et al. |
| 6,750,964 B2 | 6/2004 | Levenson et al. |
| 6,775,349 B2 | 8/2004 | Schotland et al. |
| 6,775,567 B2 | 8/2004 | Cable |
| 6,813,030 B2 | 11/2004 | Tanno |
| 6,919,919 B2 | 7/2005 | Nelson et al. |
| 6,924,893 B2 | 8/2005 | Oldenbourg et al. |
| 6,963,375 B1 | 11/2005 | Lundberg |
| 7,113,217 B2 | 9/2006 | Nilson et al. |
| 7,184,047 B1 | 2/2007 | Crampton |
| 7,263,157 B2 | 8/2007 | Bruder et al. |
| 7,603,167 B2 * | 10/2009 | Stearns et al. ................. 600/473 |
| 7,616,985 B2 * | 11/2009 | Stearns et al. ................. 600/473 |
| 2001/0019105 A1 * | 9/2001 | Wake et al. .................... 250/234 |
| 2002/0001080 A1 | 1/2002 | Miller |
| 2003/0002028 A1 | 1/2003 | Rice et al. |
| 2003/0011701 A1 * | 1/2003 | Nilson et al. .................. 348/370 |
| 2003/0099329 A1 | 5/2003 | Schotland et al. |
| 2004/0010192 A1 | 1/2004 | Benaron et al. |
| 2004/0015062 A1 | 1/2004 | Ntziachristos et al. |
| 2004/0021771 A1 | 2/2004 | Stearns et al. |
| 2004/0027659 A1 | 2/2004 | Messerschmidt et al. |
| 2004/0085536 A1 | 5/2004 | Schotland et al. |
| 2004/0262520 A1 | 12/2004 | Schotland et al. |
| 2005/0149877 A1 | 7/2005 | Rice et al. |
| 2005/0283071 A1 | 12/2005 | Ripoll et al. |
| 2006/0118742 A1 | 6/2006 | Levenson et al. |
| 2006/0119865 A1 | 6/2006 | Hoyt et al. |
| 2006/0146346 A1 | 7/2006 | Hoyt |
| 2006/0173354 A1 | 8/2006 | Ntziachristos et al. |
| 2006/0203244 A1 | 9/2006 | Nilson et al. |
| 2006/0245631 A1 | 11/2006 | Levenson |
| 2006/0268153 A1 | 11/2006 | Rice et al. |
| 2007/0016078 A1 | 1/2007 | Hoyt et al. |
| 2008/0103390 A1 * | 5/2008 | Contag et al. .................. 600/427 |

\* cited by examiner

METHOD AND APPARATUS FOR 3-D IMAGING OF INTERNAL LIGHT SOURCES

CROSS-REFERENCE TO RELATED APPLICATIONS

This application is a continuation of co-pending and commonly owned U.S. application Ser. No. 12/569,842 filed Sep. 29, 2009, which is a continuation of U.S. application Ser. No. 10/606,976 filed Jun. 25, 2003, now U.S. Pat. No. 7,616,985, issued Nov. 10, 2009, which in turn (1) claims priority under 35 U.S.C. §119(e) from U.S. Provisional Application No. 60/395,357 filed Jul. 16, 2002, (2) claims priority under 35 U.S.C. §119(e) from U.S. Provisional Application No. 60/396,458 filed Jul. 16, 2002, and (3) claims priority under 35 U.S.C. §119(e) from U.S. Provisional Application No. 60/396,313 filed Jul. 16, 2002; each of these patent applications is incorporated by reference in its entirety for all purposes.

FIELD OF THE INVENTION

The present invention relates generally to imaging with light. In particular, the present invention relates to systems and methods for obtaining a three-dimensional representation of a light source or light source distribution inside a turbid sample, which is particularly useful in biomedical imaging and research applications.

BACKGROUND OF THE INVENTION

Bioluminescent imaging is a non-invasive technique for performing in vivo diagnostic studies on animal subjects in the areas of medical research, pathology and drug discovery and development. Bioluminescence is typically produced by cells that have been transfected with a luminescent reporter such as luciferase and can be used as a marker to differentiate a specific tissue type (e.g. a tumor), monitor physiological function, track the distribution of a therapeutic compound administered to the subject, or the progression of a disease. A wide range of applications have been demonstrated including areas of oncology, infectious disease, and transgenic animals. In vivo imaging of cells tagged with fluorescent reporters is a related technology that has also been demonstrated recently in both green fluorescent protein (GFP) and near infrared (NIR) dyes such as Cy5.5.

Photons emitted by bioluminescent cells are strongly scattered in the tissue of the subject such that propagation is diffusive in nature. As photons diffuse through tissue many are absorbed, but a fraction reach the surface of the subject and can be detected. In general, absorption in mammalian tissues is high in the blue-green part of the spectrum (<600 nm) and low in the red and NIR part of the spectrum (600-900 nm). Firefly luciferase has a rather broad emission spectrum ranging from 500-700 nm, so at least part of the emission is in the low absorption region. Since the mean-free-path for scattering in tissue is short, on the order of ~0.5 mm, photons from deep sources are scattered many times before reaching the surface. Bioluminescent imaging systems effectively record the spatial distribution of these photons emitted from the surface of the subject.

However, the most important quantitative information is not directly related to the surface emission but instead pertains to the bioluminescent source inside the subject. Important parameters are the source strength (related to the number of light emitting cells), position and geometry. Most of the bioluminescent imaging work published to date involves use of single-view 2D imaging systems. Image analysis usually involves quantifying a light emitting region-of-interest (ROI) on the subject surface. While this analysis methodology is simple and provides a good relative measure of light emission, it does not take into account the source depth and resulting attenuation through tissue.

Hence, there is interest in developing both improved imaging systems and reconstruction algorithms that would provide the three-dimensional distribution of photon emission inside the sample (e.g., animal) from images measured on the sample surface.

SUMMARY OF THE INVENTION

The present invention provides systems and methods for obtaining a three-dimensional (3D) representation of one or more light sources inside a sample, such as a mammal. Mammalian tissue is a turbid medium, meaning that photons are both absorbed and scattered as they propagate through tissue. In the case where scattering is large compared with absorption, such as red to near-infrared light passing through tissue, the transport of light within the sample is described by diffusion theory. Using imaging data and computer-implemented photon diffusion models, embodiments of the present invention produce a 3D representation of the light sources inside a sample, such as a 3D location, size, and brightness of such light sources.

In one aspect, the present invention relates to a method for obtaining a three-dimensional representation of a light source distribution located inside a turbid sample. Surface light image data is provided from light emitted from a surface of the sample originating from the light source distribution located inside the sample. Light data internal to the sample surface is then obtained based on this provided surface light image data. In a specific embodiment, the surface light image data is converted into photon density just below the sample surface, and this photon density is then used to obtain the light data internal to the sample surface to thereby result in a three-dimensional representation of the light source distribution within the sample.

In yet another aspect, the present invention relates to an imaging system for obtaining a three-dimensional representation of a light source located inside a sample. The imaging system comprises an imaging chamber having a set of walls enclosing an interior cavity. The imaging chamber also includes a camera mount configured to position a camera and a moveable stage apparatus. The movable stage apparatus includes a transport mechanism and a stage configured to support the sample within the interior cavity. The stage is coupled with the transport mechanism for movement of the sample to one of a plurality of positions in the interior cavity. The imaging chamber further includes a light transport mechanism for transmitting light emitted from a surface of the sample. The imaging chamber also includes a processor designed or configured to provide surface light image data from light emitted from the surface of the sample originating from the light source distribution located inside the sample. The processor is further configured to obtain light data internal to the sample surface to obtain a three-dimensional representation of the light source distribution based on the surface light image data.

In still another aspect, the present invention relates to a computer program product. The computer program product comprises a computer readable medium and program instructions provided via the computer readable medium. The program instructions comprise reconstruction instructions for obtaining a three-dimensional representation of a light source located inside a sample. The reconstruction instructions are capable of performing one or more of the above described method operations.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

Imaging System

The 3D light reconstruction techniques of the present invention may be implemented within any suitable system. Several embodiments of imaging systems in which are suitable for implementing the techniques of the present invention are described further in U.S. patent application Ser. No. 09/905,668 filed by Nilson et al. on Jul. 13, 2001, now U.S. Pat. No. 7,113,217 issued Sep. 26, 2006, entitled MULTI-VIEW IMAGING APPARATUS. The entire disclosure of this application is incorporated herein by reference for all purposes.

Figure 1:
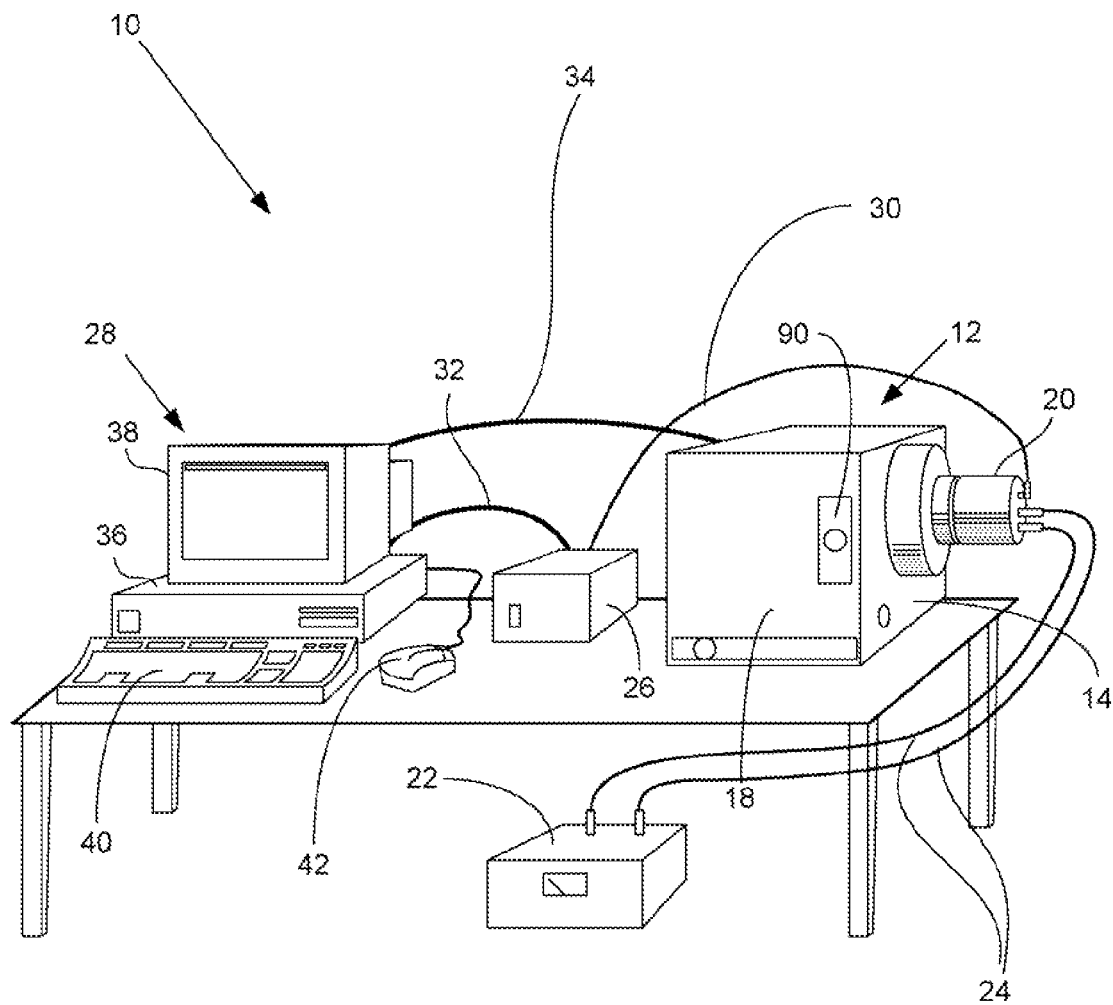
FIG. 1 is a perspective view of an imaging system adapted to produce a 3D representation of a light source located inside a sample in accordance with one embodiment of the invention.

FIG. 1 illustrates an imaging system 10 adapted to produce a 3D representation of a light source located inside a sample in accordance with one embodiment of the present invention. The imaging system 10 may be used for a variety of tasks. By way of examples, these tasks may include capturing photographic, luminescent, and structured light images. These tasks may also include performing various processing and imaging tasks such as obtaining, analyzing and manipulating 3D light source representations.

The system 10 generally images and processes low intensity light sources using a light sensitive camera. Light from the light source refers to photons and electromagnetic energy anywhere in the visible to near-infrared (NIR) part of the spectrum in the wavelength range of 400-950 nm. It is understood that some intensities imaged and processed in system 10 are not readily detectable by human vision. For example, low intensity light emitted from a sample may have a surface radiance between about $10^3$ to about $10^{10}$ photons/second/centimeter squared/steradian, where the lower end of this range is typically well below human detection levels.

In the illustrated embodiment, the imaging system 10 includes an imaging chamber 12 adapted to receive a light-emitting sample in which low intensity light, e.g., luciferase-based luminescence, is to be detected. A high sensitivity camera 20, such as an intensified or a charge-coupled device (CCD) camera, is coupled with the imaging chamber 12. The camera 20 is capable of capturing luminescent, photographic (i.e., reflection based images) and structured light images of the sample within imaging chamber 12. The camera 20 may optionally be cooled by a suitable source such as a refrigeration device 22 that cycles a cryogenic fluid through the camera via conduits 24.

An image processing unit 26 optionally interfaces between camera 20 and a computer 28 through cables 30 and 32, respectively. The computer 28, which may be of any suitable type, typically comprises a main unit 36 that contains hardware including a processor, memory components such as random-access memory (RAM) and read-only memory (ROM), and disk drive components (e.g., hard drive, CD, floppy drive, etc.). The computer 28 also includes a display 38 and input devices such as a keyboard 40 and mouse 42. The computer 28 is in communication with various components in the imaging chamber 12 via cable 34. Alternatively, a computer may be integrated with the imaging equipment in a single unit.

To provide control and communication for components in system 10, computer 28 may be implemented with any suitable combination of hardware and software for controlling and monitoring any of the devices in system 10. Components controlled by the computer 28 may include camera 20, the motors responsible for camera 20 focus, the camera lens, f-stop, one or more motors coupled to a moveable stage included in chamber 12, etc. Computer 28 also communicates with a display 38 for presenting imaging information to the user and also acts an interface to control the imaging system 10.

Computer 28 also includes suitable processing hardware and software for image processing and data manipulation as described herein. For example, computer 28 may be configured with software to build a 3D representation of a light source using light emission measurements from the surface of a sample. In addition, the computer 28 may be configured to produce 3D surface topography using 2D structured light images taken from one or more positions of the stage in the interior cavity. These 3D light construction techniques are further described below. Alternatively, the computer 28 may be integrated with the other components of the imaging system 10 to form a stand alone device.

In one implementation, the 3D light reconstruction techniques discussed further below require bioluminescent surface radiance and surface topography measurements over the entire sample surface. Thus, the imaging system also includes mechanisms for capturing images of the sample surface from a variety of views and positions. Preferably the imaging system meets the following goals. First, it is desirable for the camera to remain fixed, because the various cables and supply lines for cooling the camera are too cumbersome to move during imaging. Second, the sample preferably remains horizontal during imaging. Finally, the imaging system is preferably configured to obtain a 3D surface topography of the sample as input to the reconstruction techniques described further below. Any suitable combination of hardware and software may be used to implement these preferred goals.

Figure 2A:
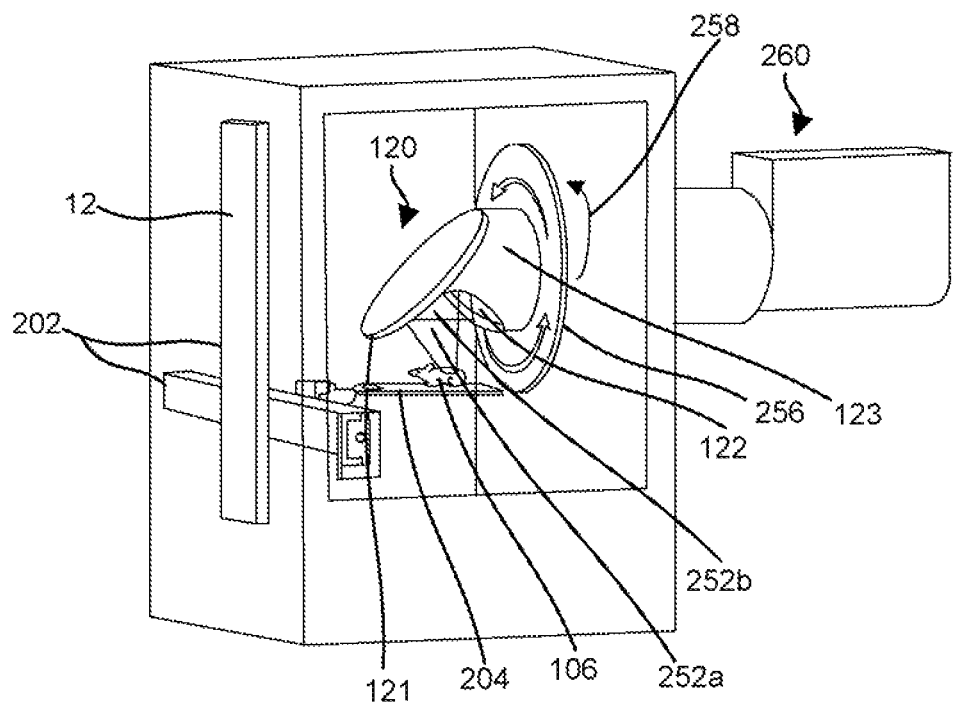
FIG. 2A is a cut away perspective view of the chamber of FIG. 1 having internal components for facilitating multiple views of the sample in accordance with one embodiment of the present invention.
Figure 2B:
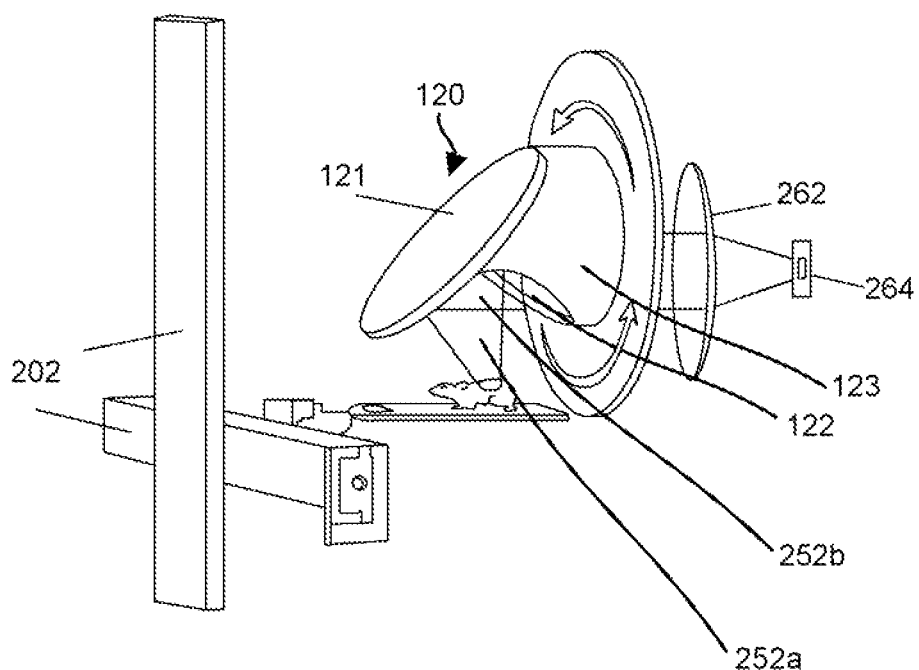
FIG. 2B is a perspective view of the internal components of FIG. 2A for facilitating multiple views of the sample in accordance with one embodiment of the present invention.

FIGS. 2A and 2B illustrate various internal components of chamber 12 for facilitating multiple view imaging in accordance with one embodiment of the present invention. FIG. 2A is a cut away perspective view of chamber 12 and its internal components, while FIG. 2B is a perspective view of the internal components of FIG. 2A in accordance with one embodiment of the present invention. In the illustrated embodiments, the sample is placed on a horizontal transparent platform that rotates in conjunction with a mirror that turns about a horizontal optical axis so as to capture light from the sample from various views and direct the captured light towards a camera for imaging.

As shown, a moveable stage apparatus is disposed in the interior cavity of chamber 12 (FIG. 2A) in the form of a stage 204 to support the light-emitting sample 106 and a transport mechanism 202 to move the stage. A light transport device 120 is included to collect light from the sample at its various positions. In the illustrated embodiments of FIGS. 2A and 2B, light emitted from the sample in the form of light beam 252a generally reflects off light transport device 120 as beam 252b. The light transport device directs this reflected light 252b through aperture 122 and through lens 262 (FIG. 2B) for image capture by a detector 264 (FIG. 2B) of camera 20 (FIG. 1).

In one implementation, light transport device 120 includes an angled mirror 121 that reflects light from the sample 106 on stage 204 through aperture 122. Outer wall 123 is substantially cylindrical and includes aperture 122 that enables light to pass from the sample 106 on stage 204 via mirror 121 to imaging lens 262 (FIG. 2B). Outer wall 123 of light transport device 120 also prevents residual light in interior cavity of chamber 12 not directly associated with the current viewing angle of stage 204 from reaching lens 262. This is partially performed by configuring mirror 121 to be sufficiently long to span the length of stage 204. As the stage is positioned at various positions about the stationary axis of the light transport device 120, outer wall 123 and mirror 121 cooperate to collect light primarily from the angular direction of stage 204 which is then reflected towards lens 262.

Figure 2C:
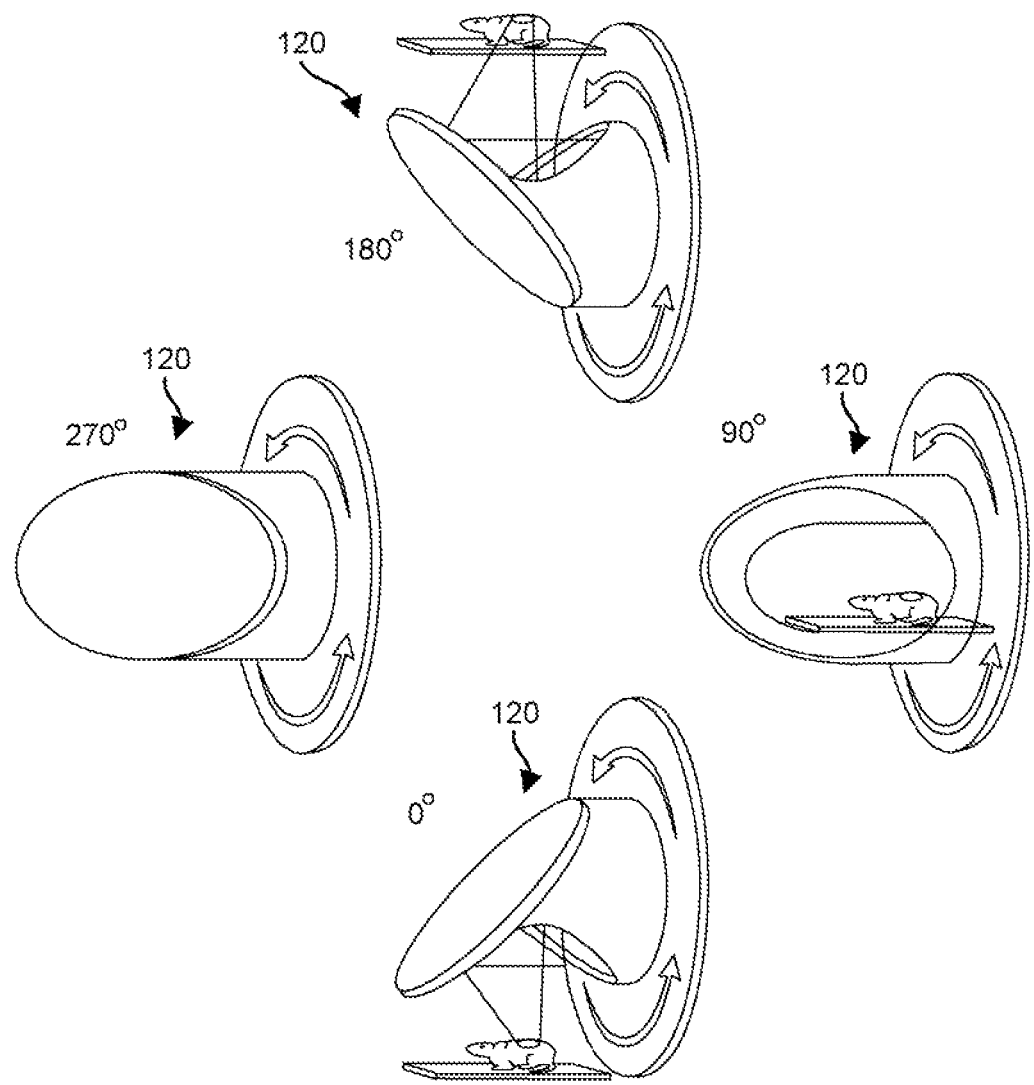
FIG. 2C shows four different example positions of the stage relative to the light transport device of FIGS. 2A and 2B: 0 degrees, 90 degrees, 180 degrees, and 270 degrees.

In the illustrated embodiment, light transport device 120 is rotably coupled to chamber 12 and rotates about a fixed axis in direction 258. The moveable stage apparatus is capable of two degrees of freedom to position the stage 204 (and sample 106) at a plurality of positions relative to the light transport device 120 so as to capture light from different sides of the sample to thereby form multiple view images of the sample. The moveable stage apparatus allows an image of the sample, or portions thereof, to be captured by a camera from different views, angles, and positions within the imaging chamber without repositioning the posture of the sample relative to the stage 204. FIG. 2C shows four different example positions of the stage relative to the light transport device (120): 0 degrees, 90 degrees, 180 degrees, and 270 degrees.

The movable stage apparatus may be formed from any suitable number, type, and arrangement of components for achieving multiple positioning and viewing of the sample. Several embodiments of a multiple-view imaging systems are described in the above referenced patent application by Nilson et al., which embodiments are incorporated herein by reference. Preferably, the movable stage apparatus also includes sensor mechanisms for sensing a position of the sample to be used in subsequent data analysis procedures as described further below.

In one embodiment, a light source is provided within the barrel of mirror assembly 120 (not shown) to illuminate the sample or specimen in the imaging chamber 12. The light source may be continuously illuminated or flashed to capture photographic images of the sample and is turned off when capturing luminescence images.

A structured light illuminator is preferably integrated into the system for reconstructing a surface topography of the sample. In a general implementation, the imaging system preferably includes a mechanism for projecting a grid of lines onto the sample from an angle, e.g., from 20 to 30 degrees from normal. The grid of lines are displaced, or phase shifted relative to the platform, when they encounter an object with finite height. Using conventional equations for structured light analysis, the surface topography data for the sample over its entire surface can be determined from the phase shift of the lines. The line spacing may vary based on the sample surface texture and sample size, but line spacing in the range of 0.5 to 2 lines per mm may be suitable for a mouse sample. Closer line spacing provides higher resolution, but the lines are more difficult to track on rough surfaces such as fur. The surface topography data is used to build a 3D representation according to the techniques described below, e.g., to set boundary conditions for the 3D reconstruction.

Figure 2D:
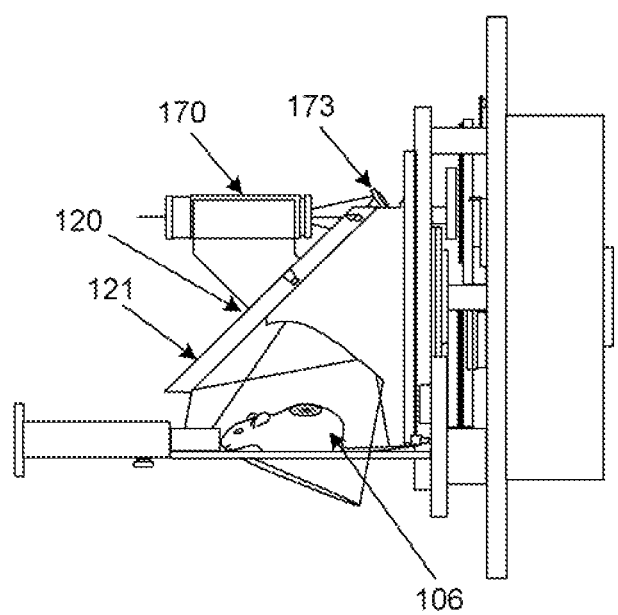
FIG. 2D shows the configuration of the structured light projector used to obtain the subject surface topography

In a specific embodiment, a simple Kohler projection scheme is used as the structured light source. In this case, the ruling may be illuminated by a diffuse LED source and the ruling is then projected onto the animal stage with a magnification of approximately 10×. An example of this system as incorporated in system 10 is shown in FIG. 2D. The projector module 170 rides on the back of the rotating mirror assembly 120, so that lines are always projected on the sample 106 at all viewing angles. The illumination pattern is projected horizontally and reflects off of a small mirror 173 at the base of the larger turning mirror to illuminate sample 106.

Figure 3A:
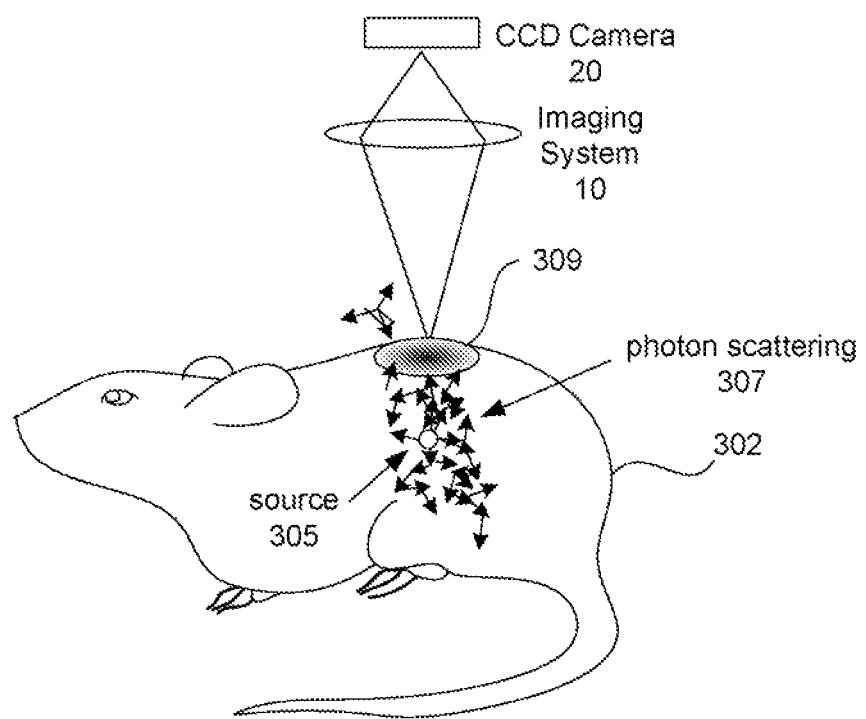
FIG. 3A shows a simplified illustration of light imaging in a turbid medium in accordance with one embodiment of the present invention.

Such an imaging system as described with respect to FIGS. 2A-2D is available from Xenogen Corporation of Alameda, Calif. Although FIGS. 2A-2D illustrate one system for obtaining data from multiple positions of sample 106 relative to camera 20, the present invention is not limited to such a system. 3D Source Reconstruction In many turbid samples such as a mammalian subject, light traveling from a light source inside the sample and emitted from the sample surface is scattered in the sample interior (e.g., the mammal tissue) such that light propagation through the sample is diffusive in nature (FIG. 3A). As the light diffuses through the sample, some of the light is absorbed, but a fraction of the light reaches the sample surface.

Emission of light from a sample surface is generally specified in units of radiance, defined as photons/sec/cm$^2$/steradian. The imaging system described herein is calibrated to report surface intensity in units of radiance. The surface radiance can be related to the photon density just inside the sample surface, using a model for photon propagation at the tissue-air interface. The photon density just inside the surface can then be related to the distribution of light emitting reporters inside the sample using a diffusion model. Thus, the present invention relates the surface radiance of a turbid sample measured with an imaging system to the distribution of light emission inside the sample. More specifically, the present invention produces a 3D representation of an internal light source using reconstruction techniques that utilize the light data emitted from the sample surface. The reconstruction techniques employ an input data set that consists of a) a topographical surface representation of the sample, and b) a set of measurements (e.g. surface images) of the light radiance over at least a portion of the surface. To facilitate processing, the surface representation may be divided into surface elements and the interior of the sample may be divided into volume elements or voxels that constitute a volume element mesh. The light source distribution within the sample is described by elements of the volume element mesh.

FIG. 3A shows a simplified illustration of light imaging in accordance with one embodiment of the present invention. FIG. 3A displays a mammalian sample 302 being imaged by an imaging system 10 that uses CCD camera 20 for light data capture. The nature of mammalian tissue and many other turbid media causes photon scattering 307 for light traveling from a light source 305 within the sample to the sample surface 309, resulting in diffuse images on surface 309. Using photon diffusion models and imaging data, the present invention produces the 3D location, size, and brightness of light source 305 from one or more surface 309 images. For user convenience, the 3D representation may be expressed as a pictorial depiction, e.g., via display 38 in FIG. 1.

One useful application of the invention is to reconstruct one or more bioluminescent or fluorescent light sources, or a source distribution, inside a living animal subject, such as a mouse, using one or more images of the surface light emission. This finds use in oncology, infectious disease research, gene expression research, and toxicology, for example. The present invention is suitable for use with samples having a complex surface, such as an animal subject (e.g. a mouse). As the term is used herein, a complex surface is any surface that cannot be described solely using a single polygonal description. The reconstruction techniques described herein place no restrictions on the source distribution, such as the number of light sources in the sample or the sizes and shapes of the sources, and no restrictions on the geometry, size or shape of the surface.

Light data internal to the sample surface generally refers to mathematical representation or approximation of actual light within the sample interior. This may include a set of points or volume elements, each characterized by 3D position and a source strength. In one embodiment, the present invention divides the sample interior into volume elements where each volume element is considered to contain a point light source at its center. A solid mesh of these volume elements then defines a collection of point sources used to approximate the actual light source distribution within the sample. For example, a solid mesh of cubic volume elements is suitable.

Figure 3B:
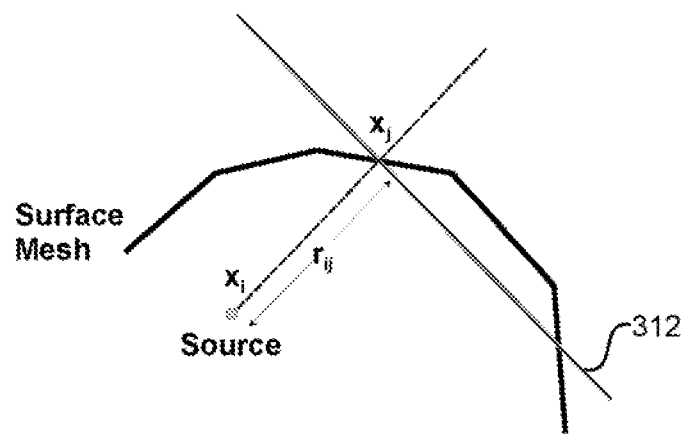
FIG. 3B illustrates a schematic diagram showing a planar approximation at the surface boundary.
Figure 3C:
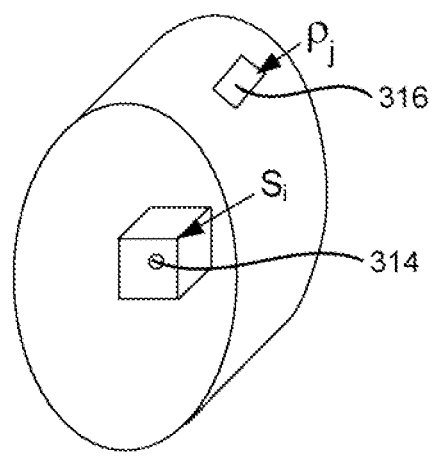
FIG. 3C illustrates the relationship between a volume element (voxel) and a surface element for a cylindrical object.

FIG. 3C illustrates an illustrative cylindrical object that is divided into a solid mesh of volume elements, one of which is shown. Each volume element contains a point light source 314, $S_i$, that contributes to the photon density 316, $\rho_j$, at the surface. For a cubic volume element representation, the volume element size may vary according to the size of the sample and a desired solution accuracy. In general, increasing the solid mesh density improves the accuracy of the internal light data representation. It is possible to have the density of the solid mesh vary with the volume of the sample. In particular, it is desirable to have the solid mesh density increase near the light source to provide a more accurate representation in this region, while density of the solid mesh decreases in areas where no activity of interest is taking place (in areas corresponding to no or minimal light generation).

The surface representation refers to the surface topography of the sample and is embodied by a mathematical description or approximation of the actual surface. The surface representation need not include the entire sample, and may include a portion of the sample relevant to a particular imaging scenario. With a mouse for example, the surface representation might not necessarily include the entire mouse such as distal portions of the tail and distal portions of every foot. Thus, the surface representation is meant to broadly refer to any surface portion of the sample and not necessarily the entire sample. Typically, the surface representation includes one or more surface elements or regions of interest on the sample that produce surface light emission data related to the internal light source. For user convenience, the surface representation is often displayed in a pictorial depiction such as a 3D depiction derived from structural light construction techniques.

The sample containing the light source comprises a turbid interior of some sort. A turbid interior in this case refers to a volume that does not allow unimpeded transport of light. The turbid interior may comprise one or more mediums, structures, solids, liquids, gases, etc. In one embodiment, the sample is modeled as homogeneous such that each representative volume element in the sample is characterized by identical light transport properties. In another embodiment, the sample is represented as heterogeneous such that various representative volume elements in the sample are characterized by different light transport properties. In a mammalian sample such as a mouse for example, the interior may comprise a mixture of tissues, bones, organs, etc., each of which may be characterized by separate light transport properties in a heterogeneous model.

The present invention presents several methods for reconstructing a three-dimensional light source distribution internal to a sample based on the surface light emission, as will be described in greater detail below. Briefly, a set of structured light and luminescent images are first acquired, e.g., obtained with a system as described above. The surface topography of the animal is reconstructed using structured light algorithms and a surface mesh is generated. Let the surface elements be enumerated with the integers j. Using one or more luminescent images, the orientation of the imaging system, and the orientation of the surface mesh, the photon density, $\rho_j$, just below the surface of the $j^{th}$ element can be determined. The photon density just below the surface is related to the light intensity emitted from the surface (Eq. 1) as will be detailed below. A set of volume elements can be constructed in the volume interior to the surface. Let the volume elements be enumerated with the integers i. The source strength in each volume element, $S_i$, is linearly related to the photon density just below the surface through a Green's function kernel, $G_{ij}$, yielding a set of linear equations (Eq. 4) as will be detailed below.

Figure 5A:
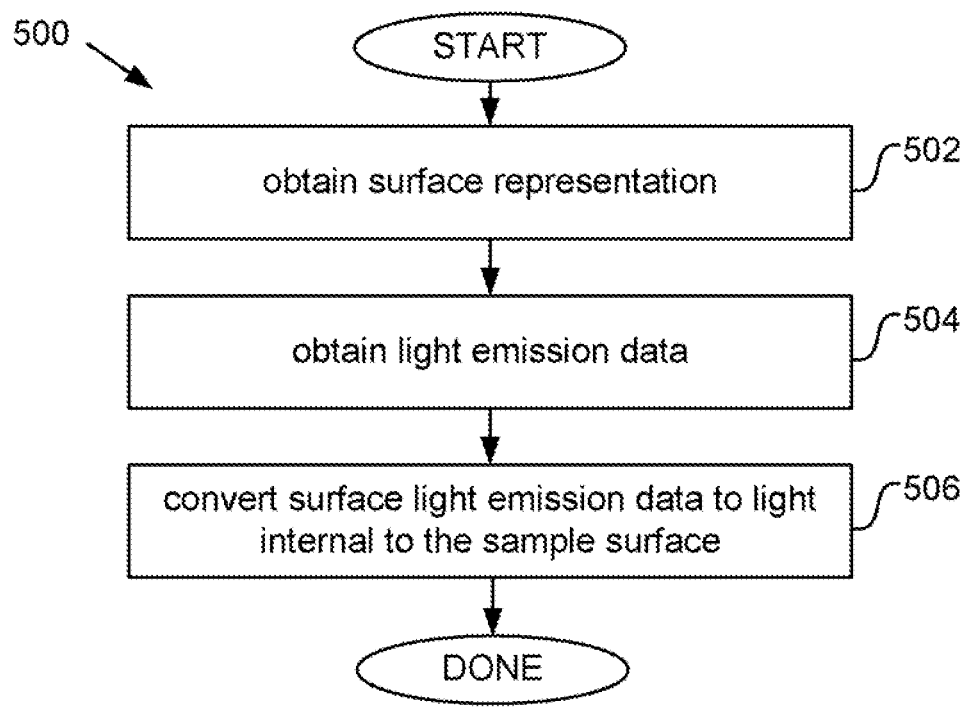
FIG. 5A illustrates a process flow for obtaining a 3D representation of one or more light sources inside a sample in accordance with one embodiment of the present invention.

FIG. 5A illustrates a process flow 500 for obtaining a 3D representation of one or more light sources inside a sample in accordance with one embodiment of the present invention. Processes in accordance with the present invention may include up to several additional steps not described or illustrated herein in order not to obscure the present invention.

Process flow 500 uses 3D reconstruction techniques that manipulate light data emitted from a sample surface. The reconstruction techniques employ data that provides information about the geometry of the sample and the spatial distribution of the light emission from the sample surface. This may include data that comprises a) a surface representation of the sample, and b) a set of measurements (e.g. images) of the light emission over at least a portion of the surface. One format for this data comprises (1) a surface representation defining the surface of the sample, (2) a set of light emission images from the sample surface, and (3) a set of parameters that define the spatial relationship between the sample and each image.

Process flow 500 begins by obtaining input data (502 and 504) used in the 3D reconstruction techniques. For example, process flow 500 may begin by obtaining a surface representation (502). To facilitate processing, the surface representation may be divided into surface elements or a suitable surface mesh approximating the actual surface of the sample (502). For example, the surface mesh may be defined by a set of connected polygons, where each polygon is a surface element. The number of surface elements may vary according to the size of the sample and a desired solution accuracy. Also the density of surface elements may vary from point to point on the surface mesh. In general, the accuracy of a surface representation is improved by increasing the number of surface elements.

Process flow may also obtain surface light emission data from the sample (504). For imaging system 10, the surface light emission data is contained in images captured by camera 20. The images include a set of measurements of the light emission over one or more portions of the surface. In one embodiment, multiple images of the sample are obtained from multiple views of the sample relative to the camera. In this case, each image provides a different two-dimensional view of the surface light emission from the sample. Multiple images may be taken to provide additional data from multiple angles.

The image data may then be mapped back onto the surface of the sample. Since a camera produces 2D data, the image data is manipulated according to the geometry between the sample surface and the camera lens to derive values of the light emission intensity (or radiance) at the surface.

Figure 4A:
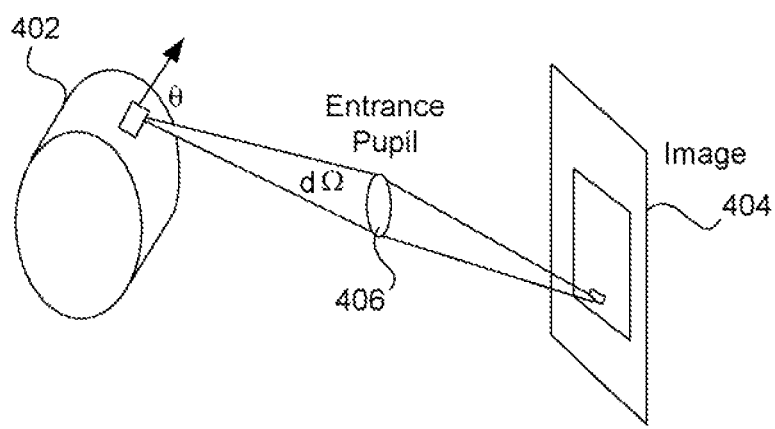
FIG. 4A illustrates exemplary relationships for converting between 2D camera data and surface data for an exemplary surface element.

FIG. 4A is an illustrative relationship for converting 2D camera data to surface data for an exemplary surface element 402. FIG. 4A shows the relationship between surface element 402, image 404, and an entrance pupil 406 of the imaging system. The light emitted from surface element 402 passes through entrance pupil 406 and is recorded in image 404. The angle of emission with respect to the surface normal is $\theta_2$. The entrance pupil 406 subtends a small solid angle $d\Omega$. Imaging system 10 may collect light emitted from a surface element 402 on the sample at an angle $\theta_2$ (measured with respect to the normal to surface element 402) into the solid angle $d\Omega$ subtended by the entrance pupil. This information may then be used to convert image data obtained by the camera into the surface emission intensity corresponding to the surface geometry.

Process flow 500 then converts the surface light emission data into light data internal to the surface to obtain the three-dimensional representation (506). The surface emission intensity is related to the photon density just inside the sample surface. The present invention thus converts values of light emission intensity for each surface element into photon density just inside the surface. Referring again to FIG. 4A, the value of emission intensity at a surface element, $I(\theta_2)$, is related to the photon density $\rho$ beneath the surface element. The exact form of the relationship depends on the model used to describe the transport of photons across the surface boundary. One embodiment of this relationship, based on the partial-current boundary condition [Haskell, et al.], is given by:

$$I(\theta_2) = \frac{c}{4\pi n^2}T(\theta)\cos\theta_2 d\Omega\left[1 + \frac{3}{2}\frac{1-R_{eff}}{1+R_{eff}}\cos\theta\right]\rho \quad (1)$$

Here, c is the speed of light, n is the index of refraction of the sample medium, T is the transmission coefficient for light exiting the sample through the surface element, and $\theta$ is the internal emission angle, which is related to the external emission angle $\theta_2$ through Snell's law:

$$n\sin\theta = \sin\theta_2 \quad (2)$$

The parameter $R_{eff}$ is the average internal reflection coefficient calculated from the following formulae:

$$R_{eff} = \frac{R_\phi + R_j}{2 - R_\phi + R_j} \quad (3)$$

$$R_\phi = \int_0^{\frac{\pi}{2}} 2\sin\theta\cos\theta R(\theta)d\theta$$

$$R_j = \int_0^{\frac{\pi}{2}} 3\sin\theta\cos^2\theta R(\theta)d\theta$$

$$R(\theta) = \begin{cases} \frac{1}{2}\left(\frac{n\cos\theta_2 - \cos\theta}{n\cos\theta_2 + \cos\theta}\right)^2 + \frac{1}{2}\left(\frac{n\cos\theta - \cos\theta_2}{n\cos\theta + \cos\theta_2}\right)^2 & \text{for } \theta < \arcsin(1/n) \\ 1 & \text{for } \theta > \arcsin(1/n) \end{cases}$$

Thus, the internal reflectivity $R_{eff}$ depends on the index of refraction of the medium underneath a surface element. In tissue for example, $R_{eff}$ is typically in the range of 0.3-0.5.

Eqs. (1) and (2) may thus be used to convert surface emission data measured at each surface element to values of the photon density beneath the surface. As the term is used herein, the subscript j enumerates a set of surface elements. $\rho_j$ is then the value of the photon density calculated at the jth surface element. Further description of the conversion between surface light emission data into light data internal to the surface to obtain the three-dimensional representation is provided in FIG. 5D.

Figure 5B:
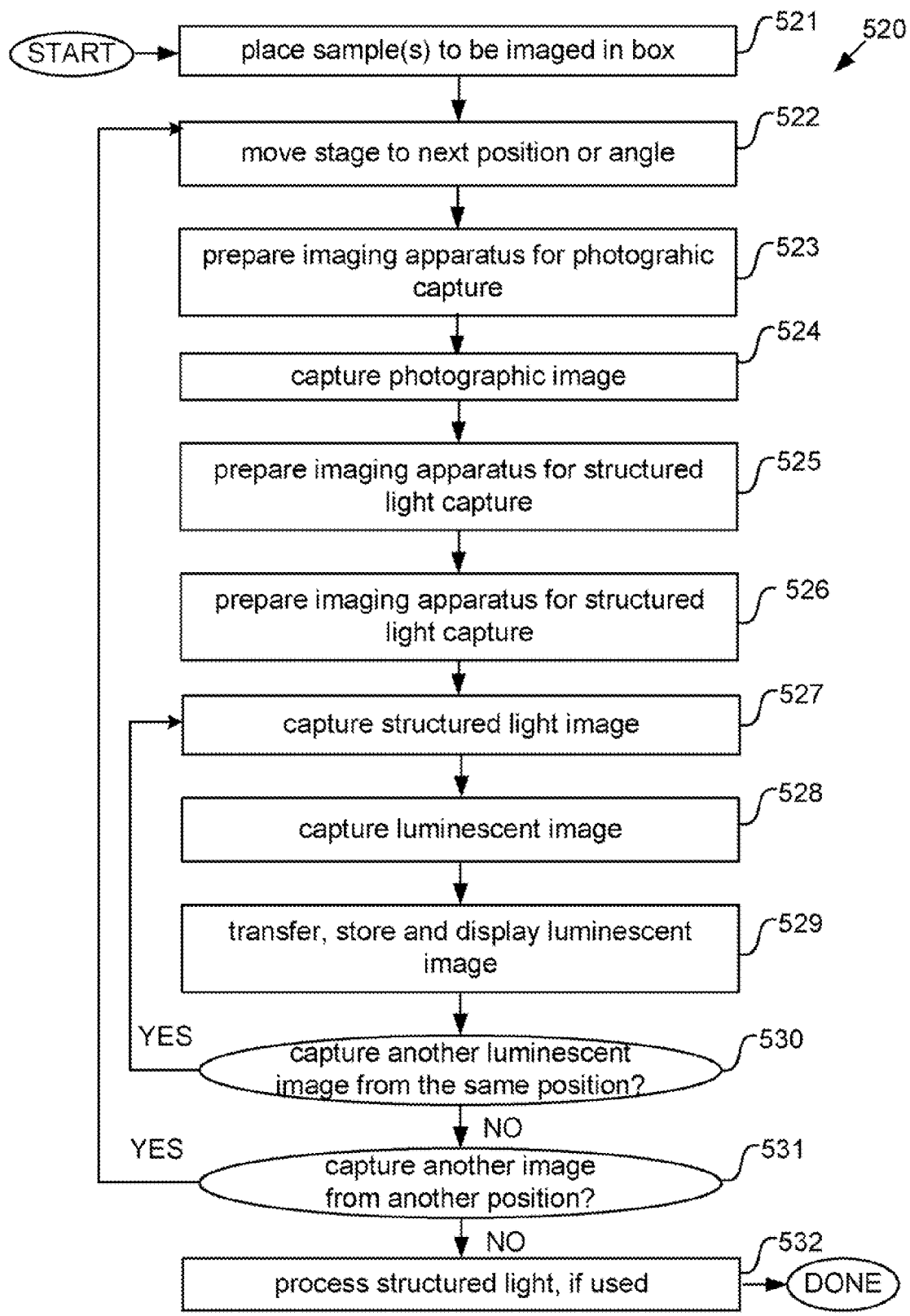
FIG. 5B illustrates a process flow for using the imaging system of FIG. 1A to obtain imaging data in accordance with one embodiment of the present invention.

FIG. 5B illustrates a process flow 520 for using imaging system 10 of FIG. 1 to obtain imaging data in accordance with one embodiment of the present invention (504 from process flow 500). Process flow 520 begins by placing a sample such as a specimen or assay to be imaged for light emission on stage 204 within imaging chamber 12 (521). Using computer 28, a user inputs a desired position for stage 204. Alternatively, the desired position for stage 204 is already known based on an automated data collection method. Transport mechanism 202 moves stage 204 to the desired position according to a control signal provided by computer 28 (522). Light transport device 120 may also re-position according to a control signal provided by computer 28. Imaging chamber 12 and associated image components are then prepared for photographic image capture of the sample (523). Preparation may include launching imaging and acquisition software (e.g., "LivingImage" as provided by Xenogen Corporation of Alameda, Calif.) on computer 28 and initializing camera 20. Further preparations may include closing door 18, activating the photographic capture option in the software, focusing camera 20 to a specific depth of the sample or animal, and turning on the lights in chamber 12. Preparations may also include focusing the lens of camera 20, selectively positioning an appropriate the lens filter of camera 20, setting the f-stop of camera 20, etc.

A photographic image is then captured (524). In an alternative embodiment, a "live mode" is used during photographic imaging of the sample to observe the sample in real time. The live mode includes a sequence of photographic images taken frequently enough to simulate live video. Upon completion of photographic capture, the photographic image data is transferred to an image processing unit 26 and/or a processor in computer system 28. These may be used to manipulate and store the photographic image data as well as process the data for display on computer monitor 38.

In one embodiment, the present invention uses structured light during image capture. Thus, with stage 204 at a desired position, a structured light image may be captured (526). Structured light image capture may be accomplished using a structured light projection system as described above, and may also include preparation of the structured light projection system (525) and any other components of imaging system 10 used in the structured light image capture. Upon completion, the structured light image data is transferred to an image processing unit 26 and/or a processor in computer system 28, which may be useful in building a 3D representation of the sample.

Subsequently, with stage 204 at a desired position or at the same position as a previously taken photographic or structured light image, the imaging apparatus 10 is prepared for luminescence image capture (527). Such preparation may include selecting luminescent exposure time and binning level using the computer 28, and turning off the lights inside chamber 12. When ready, the CCD camera 20 then captures (514) the luminescence image over a set period of time (up to several minutes). The luminescence image data are transferred to the image processing unit and/or a processor in computer 28.

At this point, a user may manipulate and store the luminescence image data as well as process it for display on the computer display 38. The manipulation may also include overlaying the luminescent image with the photographic image and displaying the two images together as a 2-D "overlay" image, with the luminescence data typically shown in pseudocolor to show intensity. As mentioned, the photon emission data may represent the specific pixels on the camera 20 that detect photons over the duration of the image capture period. This overlay image may then be the basis for user analysis; and may be analyzed and manipulated as desired. In particular, an analysis may include a summation of the illumination magnitudes over the pixels within a portion of the luminescence representation. Note that although the discussion will focus on a single luminescence representation for the overlay image, the process flow 520 may include taking multiple luminescence representations from the same position of stage 204, e.g., at the same time or a later time (530).

Stage 204 may then be moved to a second position (531). While the stage is at the second position, one or more photographic, structured light, and/or luminescence images of the sample may be captured as described above. Image collection may further continue by capturing images of the sample from alternate positions and views of the sample. For 3D reconstruction, photographic, structured light, and/or luminescence images of the sample may be captured from a number of positions. For example, image capture may occur at anywhere from 2 to 200 positions of the sample within the imaging chamber. The preferred number of images is 8, spaced every 45 degrees. In one embodiment, this process is automated and controlled via computer 28.

After a suitable number of structured light images have been captured from various angles and stored, computer 28 may then process the structured light data from each angle to generate a structured light representation (532). Each structured light image provides the surface topography for approximately the facing half of the sample.

In another embodiment, process flow 520 and imaging apparatus 10 reconstruct the 3D surface topography of the sample using a sequence of images. By taking images from several viewing angles, e.g., about every 45 degrees, the entire 3D surface of the sample can be reconstructed by "stitching" together the partial surface reconstructions obtained from each view. A sequence of images may then be taken at different viewing angles and used in reconstructing the sample's 3D surface topography. The 3D surface topography and image data may also be used in reconstructing the 3D location, brightness, and size of the light source within the sample. Once the images are received by processor 28, a suitable reconstruction algorithm is applied to the data to obtain the 3D surface topography. As one of skill in the art will appreciate, there are numerous algorithms for reconstructing a surface from structured light images. For example, the phase shift of each line at all points on the image can be determined from a 2D Fourier transform. Such a process is described in detail in the article entitled "Fourier-transform method of fringe-pattern analysis for computer-based topography and interferometry," by M. Takeda, H. Ina and S. Kobayshi, JOSA 72, 156-160 (1982), which article is incorporated herein by reference in its entirety. The actual surface height is then computed by "unwrapping" the phase map. Such a process is described in detail in the textbook entitled "Two-Dimensional Phase Unwrapping, Theory, Algorithms, and Software" by D. C. Ghiglia and M. D. Pritt, (John Whiley and Sons, New York, N.Y., 1998), which textbook is incorporated herein by reference in its entirety. Together, a structured light photographic representation of the sample and a luminescence representation of the sample may be combined to form a structured light superposition or 3D overlay image, with the luminescence data typically shown in pseudocolor to visually characterize intensity.

Figure 4B:
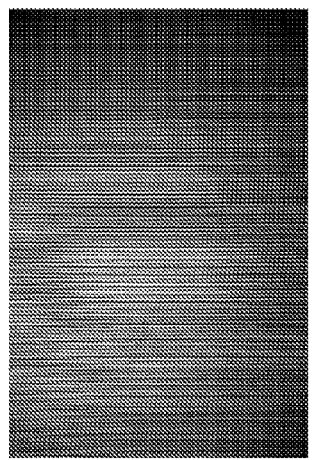
FIGS. 4B-4H illustrate pictorial representations of structured light imaging corresponding to the process flow of FIG. 5C.
Figure 4C:
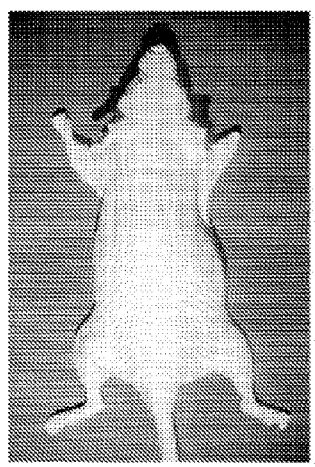
Figure 4D:
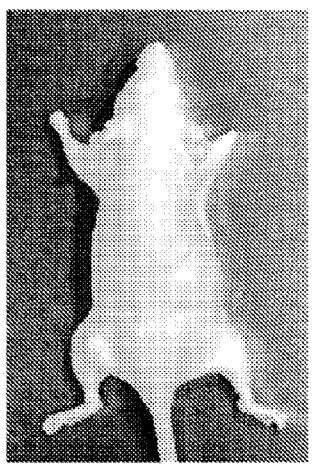
Figure 4E:
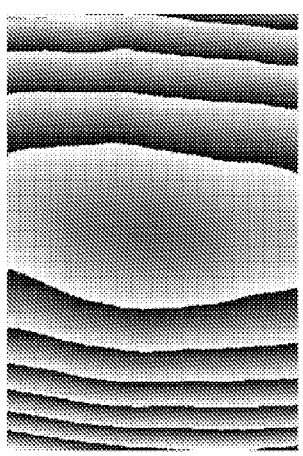
Figure 4F:
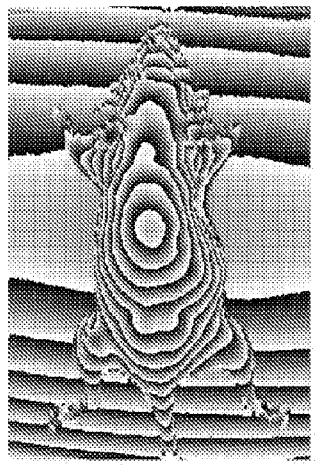
Figure 4G:
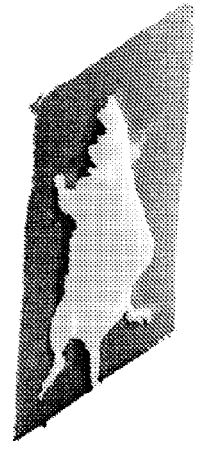
Figure 4H:
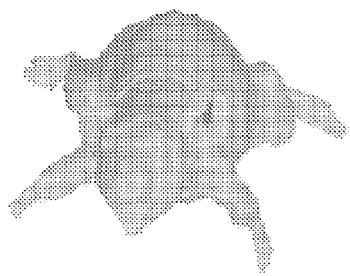
Figure 5C:
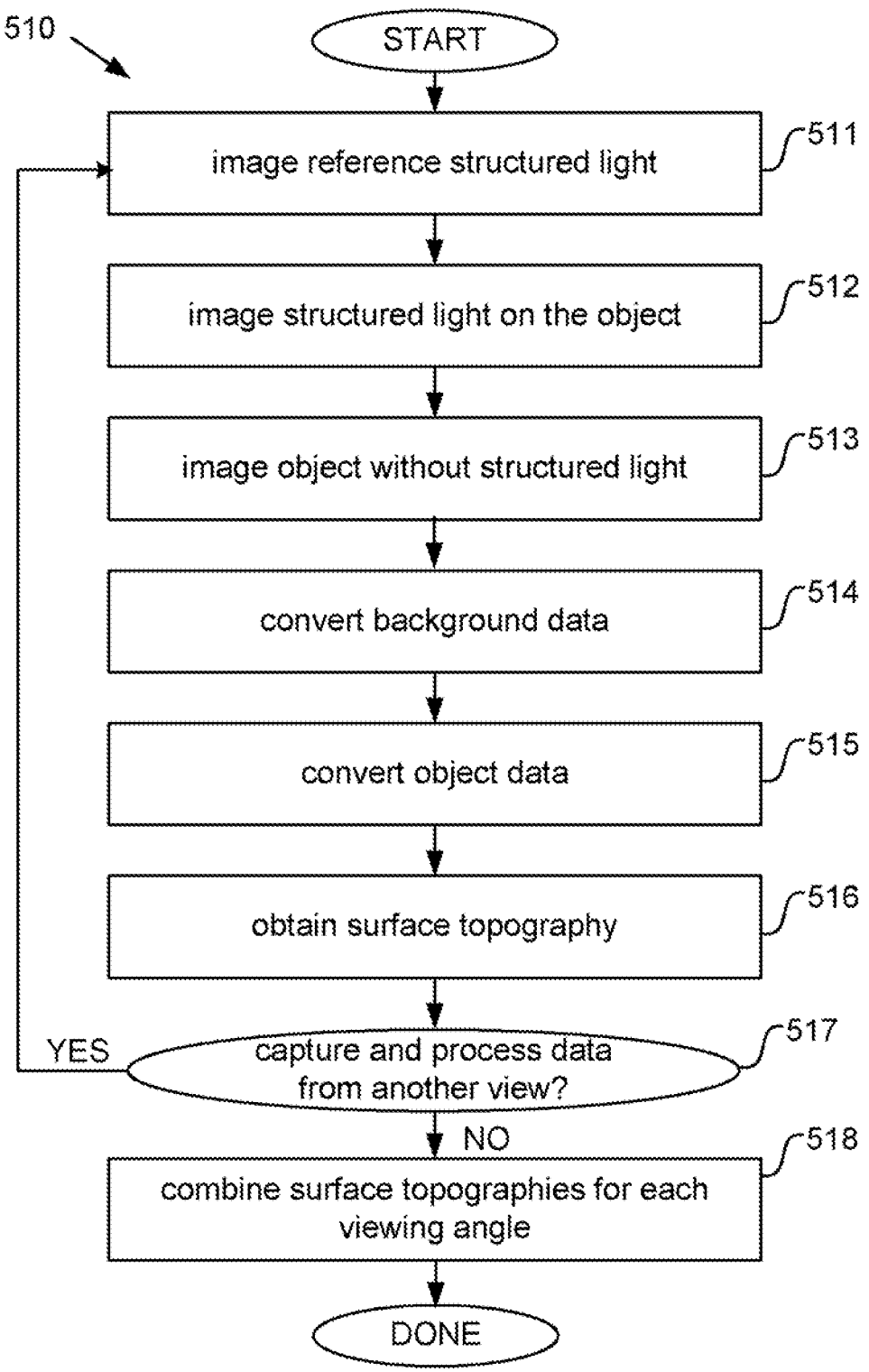
FIG. 5C illustrates a process flow for using the imaging system of FIG. 1A to obtain surface topography data in accordance with one embodiment of the present invention.

FIG. 5C illustrates a process flow 510 for using imaging system 10 of FIG. 1 to obtain surface topography data in accordance with another embodiment of the present invention (502 from process flow 500). FIGS. 4B-4H illustrate pictorial representations of structured light imaging corresponding to process flow 510.

Process flow 510 begins by imaging a structured light reference to produce a pattern without the sample (511 and FIG. 4B). This may be performed by applying structured light to a stage or surface that the sample rests upon before the sample is imaged. During image capture of the sample, the stage is moved to common locations as those used in image capture without the sample.

Subsequently when the sample is in the imaging chamber, the sample is imaged with structured light (512 and FIG. 4C). Structured light uses a series of lines of light that are projected down on a sample at an angle (at about 30 degrees, for example) to the surface normal. The lines bend as they pass over the sample, and the bend in the lines can be used to determine the height of the surface at all locations that are illuminated by a structured light projector (such as structured light projector 170 described above). As shown in FIG. 2D, structured light projector 170 is attached to and rotates with light transport device 120. In this case, structured light projector 170 consists of a Kohler illumination system where a slide is illuminated by a light source and then an image of the slide is projected onto the sample or background. The projection angle is large enough to get sufficient "bend" in the lines to achieve spatial resolution, but small enough that large shadows are not present.

Process flow 510 then proceeds by imaging the sample without structured light (513 and FIG. 4D). This may correspond to photographic image capture (524) as described above. The phase shift of each line at all points on the background and sample may be determined from a 2D Fourier transform.

The background data is then converted to a wrapped phase (514 and FIG. 4E). Here, the background data is Fourier transformed and filtered before a wrapped phase is calculated. Similarly, the sample data is converted to a wrapped phase (515 and FIG. 4F) by Fourier transforming and filtering the sample data, and the calculating a wrapped phase for the sample data.

Surface topography for the sample is then calculated (516 and FIG. 4G). In this case, this is performed by "unwrapping" the phase map. Several unwrapping algorithms are available to those of skill in the art for this task. For example, the phase shift of each line at all points on the image can be determined from using Fourier profilometry techniques. With these methods, a 2D Fast-Fourier transform (FFT) of the fringe data (FIG. 4D) is taken to determine the phase shift of the lines everywhere in the image (FIG. 4F). Since the phase will shift by many multiples of $2\pi$ for a typical object, the phase exhibits $2\pi$ jumps as seen in FIG. 4F. These phase jumps are "unwrapped" in order to determine the actual surface.

The above processes (511-516) may then be repeated (517) from different views and positions. Imaging a sample from multiple views provides additional information that helps techniques described herein provide a more accurate 3D surface rendering. The multiple images, or the partial surfaces obtained from each view in the 3D imaging system, are then registered together to form a complete 3D surface (518 and FIG. 4H). Registering can be accomplished by using non-linear least squares fitting techniques to minimize the distance between mesh elements on two surfaces that are to be connected. Typically, the surfaces should have a starting orientation that is fairly close to the final registered position. In other words, only fine adjustments to the surface positions may be accommodated with this method. Another registration technique is to provide an absolute reference line or fiducial of some kind in the image, which gives the absolute position of any partial surface with respect to the stage, for example. If the absolute positioning of each surface is accurate enough, then the non-linear fitting method described above can be skipped.

Figure 5D:
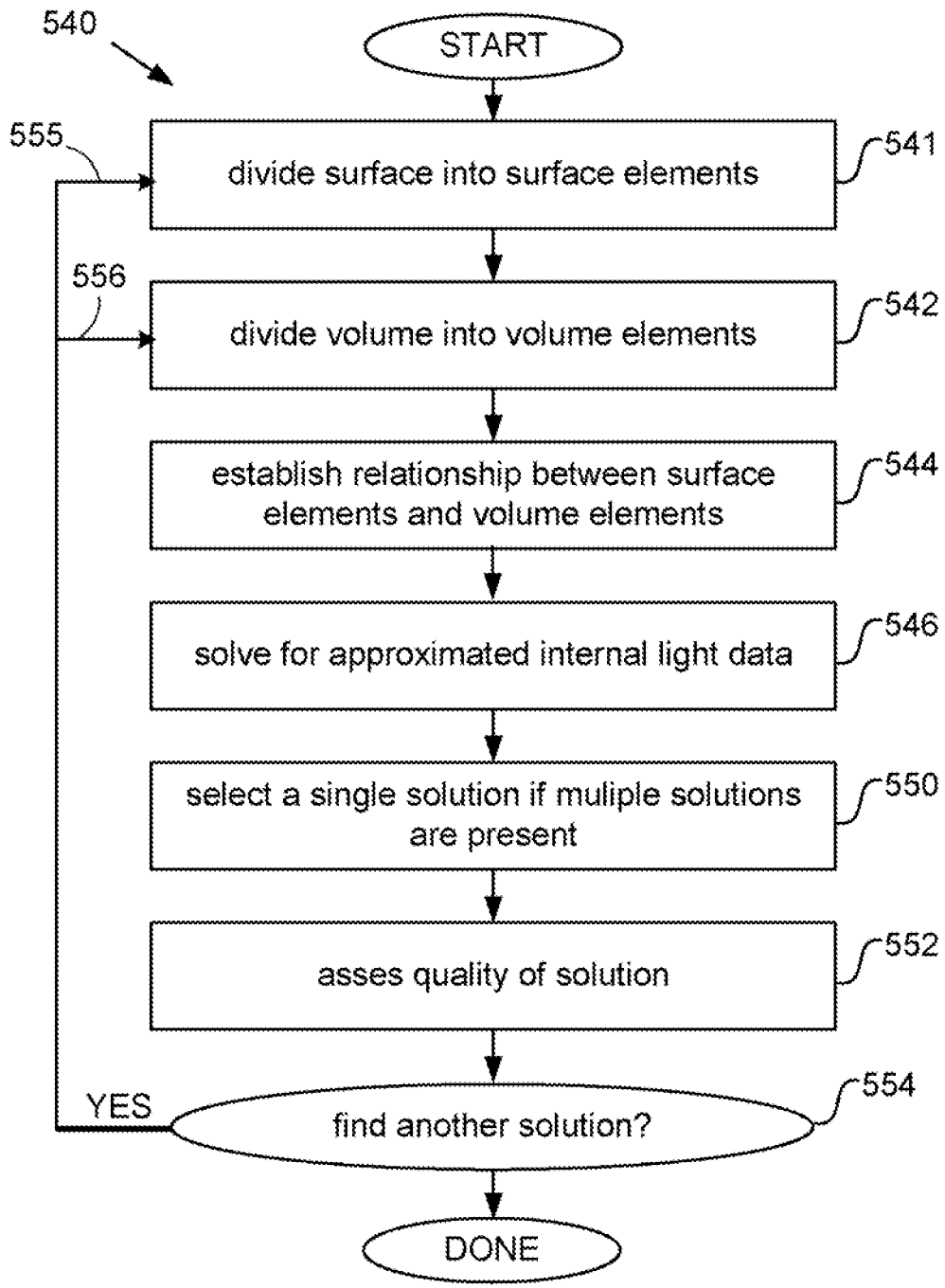
FIG. 5D illustrates a process flow for converting surface light emission data to light internal to the surface in accordance with a specific embodiment of the present invention.

FIG. 5D illustrates a process flow 540 for converting surface light emission data to a reconstruction of the light source distribution within the volume of the object in accordance with a specific embodiment of the present invention. Processes in accordance with the present invention may include up to several additional steps not described or illustrated herein in order not to obscure the present invention.

Process flow 540 assumes possession of a surface representation for the sample and possession of light emission data from the sample. Process flow 540 begins by dividing the surface representation into surface elements (541). The number of surface elements will vary according to the sample surface area and the desired solution accuracy. The number of surface elements should be large enough to capture photon density details and variation across the surface. For example, between about 100 and about 10,000 surface elements may be suitable for a mouse.

In addition, process flow 540 divides the sample interior volume into volume elements (542). In one embodiment, each volume element is considered to contain a point light source at its center. A solid mesh of volume elements then defines a collection of point sources used to approximate the actual light source distribution. In some cases, the density of the solid mesh increases near the light source to provide increased information in this space, while density of the solid mesh decreases in areas where no activity of interest is taking place (no light generation or transport). In addition, as will be described below with respect to loop 556, the volume element size may vary during solution attainment according to various adaptive meshing techniques. For example, the initial volume element size may range from about $0.1$ cm$^3$ to about $1$ cm$^3$, and the final volume element size for volume elements close to the source may reduce from about $1*10^{-3}$ cm$^3$ to about $1*10^{-2}$ cm$^3$. In a specific example, the initial volume element size may be about $1$ cm$^3$, and the final volume element size for volume elements close to the source may reduce to about $8*10^{-3}$ cm$^3$.

Process flow 540 then establishes a relationship between the surface elements and volume elements (544). In one embodiment, the reconstruction method uses a linear relationship between the source emission strength and the photon density at the surface. In a specific embodiment, the linear relationship is described by a Green's function. The Green's function contains all of the information about the transport of photons inside the sample, including the effects of inhomogeneities in the volume and internal reflection at the boundary. The Green's function describes the transport of photons inside the sample from each point in the source distribution to the inside of each surface element of the sample.

When the medium inside the sample is assumed or modeled as homogeneous, one useful form for the Green's function is a simplified approximation in which the surface of the sample is treated locally as a planar interface oriented perpendicular to a line connecting a volume element center and a surface element. The photon density at the surface is the analytical solution for a point source in a semi-infinite slab using the partial-current boundary condition. Since the solution is only a function of the distance between the volume element and the surface, the simplified Green's function can be calculated for all pairs of volume elements and surface vertices with minimal computational expense.

With a linear relationship between the source strength in each volume element and the photon density at each surface element described by a Green's function $G_{ij}$, the photon density at the jth surface element may be approximated by the sum of the contributions from all the volume elements:

$$\rho_j \cong \sum_i G_{ij} S_i \qquad (4)$$

where the index i enumerates the volume elements and $S_i$ is the value of the strength of the point source (photons/sec) inside the ith volume element.

Light transport in turbid media such as tissue is dominated by scattering and is essentially diffusive in nature. The condition for diffusive transport is that the scattering coefficient $\mu_s$ be greater than the absorption coefficient $\mu_a$ so that the change in the photon density is small between scattering events. The photon density produced by a source power density, $U_i$, in a homogeneous medium may be represented by the diffusion equation:

$$D\nabla^2 \rho - \mu_a c \rho = -U_i(\underline{x}) \tag{5}$$

where the diffusion coefficient D is, $$D = \frac{c}{3(\mu_A + \mu_S')} \tag{6}$$

In this case, the Green's function is the solution to Eq. (5) subject to the boundary condition imposed by the surface of the sample. For a sample modeled as homogeneous, a useful approximate solution for the Green's function uses a planar approximation at the surface boundary.

FIG. 3B illustrates a schematic diagram showing this planar approximation. A plane boundary 312 is drawn through the center of the jth surface element, perpendicular to the line connecting the point source at x, and the surface element at $x_j$. The photon density in the planar approximation is the solution for the point source at $x_i$ in a semi-infinite slab defined by the plane boundary, subject to the partial current boundary condition. In this case, the surface of the sample is treated locally as a simple planar boundary oriented perpendicular to the line connecting the source at $x_i$ and the surface element at $x_j$. Specifically, the boundary condition is simplified to the case of a plane boundary, although the orientation of the boundary may change for each surface element.

This simplified Green's function is the analytical solution for a point source in the semi-infinite slab using the partial-current boundary condition:

$$G_{ij} = \frac{1}{2\pi D} \left\{ \frac{\exp(-\mu_{\text{eff}} r_{ij})}{r_{ij}} - \frac{1}{z_b} \exp(r_{ij}/z_b) E_1 \left[ \left( \mu_{\text{eff}} + \frac{1}{z_b} \right) r_{ij} \right] \right\} \tag{7}$$

Here $r_{ij} = |x_j - x_i|$, $E_1$ is the first order exponential integral and $$\mu_{\text{eff}} = [3\mu_A(\mu_A + \mu_S')] \tag{8}$$

$$z_b = \frac{2D}{c} \frac{1 + R_{\text{eff}}}{1 - R_{\text{eff}}} \tag{9}$$

In the simplified model just described, the simplified Green's function depends only on the distance between the volume element and the surface. It is not necessary to use an analytical form such as the simplified approximation to define the Green's function.

The present invention does not rely on an analytical form such as the approximation described above. In another embodiment, a look-up table may define the Green's function. The look-up table may be created by previous measurements of photon transport in a sample (or similar sample approximated to be substantially equal to the current sample), or by computational simulations using techniques such as Monte Carlo or finite element modeling. This particular method is useful for samples consisting of inhomogeneous media, such as animal subjects. In this case, the optical properties, $\mu_a$ and $\mu_s$ from Eq. 8, now have spatial dependence.

The planar boundary approximations discussed above work best for smooth surfaces with a large radius of curvature, and for cases where the absorption coefficient is not too small ($\mu_a > 0.1$ cm$^{-1}$). An advantage of the planar approximation technique described above is that it is computationally convenient for solving the diffusion equation with an arbitrary complex boundary such as a mouse. Areas with more structure, such as the head or the limbs of a mouse, may benefit from a more accurate model of the boundary. Using a finite element modeling code to calculate the Green's functions is one option to obtain a more accurate boundary model. Finite element codes such as Flex PDE, from PDE Solutions, Inc. may be used for example. Another option will be to extend the planar surface approximation to first order in curvature, which may allow continued use of analytic expressions for $G_{ij}$.

Once the Green's function is determined, the reconstruction is obtained by solving the system of linear equations that relate the photon density at the surface to the source distribution inside the object. Process flow 540 then proceeds by solving for all the internal volume elements (546). More specifically, given the modeling described above, the reconstruction techniques solve the system of linear equations that relate the photon density at the surface to the source distribution inside the sample. Thus, once the Green's function is determined, it may be evaluated for every volume element-surface element pair, in order to obtain the system of linear equations (Eq. 4). The final step of the reconstruction method is to solve the linear system, Eq. (4), for the source strengths $S_i$. Referring back to Eq. (4), since $\rho$ is known, and $G_{ij}$ can be determined as described above, the reconstruction techniques then solve for $S_i$. Typically, there is no exact solution to the linear system because the collection of point sources is only an approximation of the actual source distribution. One suitable reconstruction is then the best approximate solution of the linear system.

In one embodiment, the linear system is converted into an optimization problem to find an approximate solution. In this case, a cost function is used to define the optimization problem. One suitable cost function may be represented by the sum of the source strengths:

$$\text{Cost} = \sum_j S_j \tag{10}$$

The cost function is subject to one or more linear constraints. A first suitable set of constraints is that the source strengths be positive definite:

$$S_i \geq 0 \tag{11}$$

A second suitable set of constraints is a system of linear inequalities based on the system of linear equations (4). It requires that the contributions to the photon density summed over all the volume elements be less than the measured value of the photon density at each surface element:

$$\sum_j G_{ij} S_j \leq \rho_i \tag{12}$$

In a specific embodiment, an optimum solution for source strengths $S_i$ is found by maximizing the cost function (10) subject to constraints (11) and (12).

Process flow 540 then solves for the current optimal solution in the set of solutions (550). The optimization problem described above may be solved using linear analysis techniques. One particularly efficient technique is the SIMPLEX method.

The solution quality may be assessed (552). In one embodiment, the assessment measures the difference between the observed photon density and the calculated photon density. For example, a "chi squared" criteria may be used:

$$\chi^2 = \sum_j \left[ \frac{\rho_j - \sum_i G_{ij} S_i}{\rho_j} \right]^2 \qquad (13)$$

The value of $\chi^2$ measures the difference between the observed photon density $\rho_j$ and the calculated photon density $$\sum_i G_{ij} S_i$$

over the surface of the sample.

Determination of internal 3D light source distribution data based on surface light emission data may be embedded in one or more iteration loops. Iteration may allow for refinement of the volume mesh and may allow searches for the optimal sampling of the surface elements and the optimal weighting function configuration. In general, the convergence of the reconstruction is improved by reducing the size of the linear system. In one embodiment, reconstruction techniques of the present invention iteratively vary one or more of: the volume element configuration, the surface element configuration, and/or the cost function configuration.

Iteration may also assist solution attainment. The SIMPLEX method converges rapidly to a solution, and hence has the advantage of being a computationally efficient algorithm. To assist the SIMPLEX algorithm in finding the global maximum, and hence the optimum solution, the SIMPLEX calculation may be repeated numerous times while systematically varying key elements in the algorithm (554). This can be achieved by using adaptive meshing, or adaptive gridding, to vary the number of volume elements, and by using a subset of the surface elements.

Loop 556 (FIG. 5D) illustrates repeating the solution steps while varying the number of volume elements. Typically, it is advantageous to reduce the number of volume elements in the problem while maintaining a high density of volume elements in the vicinity of the source. This can be achieved by using adaptive meshing. In one suitable adaptive meshing application, a coarse volume element mesh is initially applied throughout the entire sample volume and the current solution is found (544, 546, and 550), yielding an initial solution for $S_i$. Next the volume elements that have source strengths greater than zero ($S_i > 0$) are refined (i.e. subdivided) and those where the source strengths equal zero ($S_i = 0$) are removed. Solution attainment and volume element mesh refinement may then be iterated repeatedly, producing a high-density volume element mesh localized in the source region. During each iteration, the quality of the current solution is assessed (552). In a specific embodiment, the iteration continues until further refinement produces no significant decrease in the value of $\chi 2$.

An additional iterative improvement may be obtained by varying the number of surface elements, $N_S$, used in obtaining the three-dimensional representation (loop 555). Using a subset of the surface elements of the surface mesh reduces the number of constraints in the problem, which may simplify solution calculation. The number of surface elements may be used to sample the surface uniformly. In this case, process flow 540 iterates for different values of $N_S$ corresponding to sampling the surface element mesh at different densities, and use the quality assessment (552) to determine the best solution among the different values of $N_S$. For example, if the number of surface elements is between about 100 and about 300 surface elements for a small mouse, an iteration step size between about 10 and 50 may also suitable.

Another iteration loop varies a cost function to improve solution obtainment. For example, the cost function may be modified to include a weighting factor $W_i$:

$$\text{Cost} = \sum_i S_i / W_i^\gamma, \quad W_i = \sum_j G_{ij} \qquad (14)$$

The weighting factor W, is the contribution of the $i^{th}$ volume element to the photon density over the entire surface. The exponent $\gamma$ adjusts the relative contribution to the cost function of the interior volume elements and those volume elements close to the surface. When $\gamma=0$, then the interior volume elements have relatively greater weight. When $\gamma=1$ the volume elements near the surface have greater weight. Process flow 540 may be iterated while varying $\gamma$ to search for solutions where the source is both near and far from the surface. For example, the step size may be varied by about 0.01 to about 0.2 for a range of $\gamma$ from 0 to 1. In a specific embodiment, the step size was varied by about 0.05 for a range of $\gamma$ from 0 to 1. Once again, quality assessment (552) may be used to identify the best solution.

In a specific embodiment, the SIMPLEX calculation is imbedded in a search routine that consists of two optimization loops. The inner loop uses adaptive gridding to optimize the configuration of the volume mesh. The outer loop searches for the optimum values of the parameters $N_S$ and $\gamma$. Each step of the search algorithm is tested using the chi-squared criteria. The global solution is defined as the one that minimizes $\chi^2$.

Figure 5E:
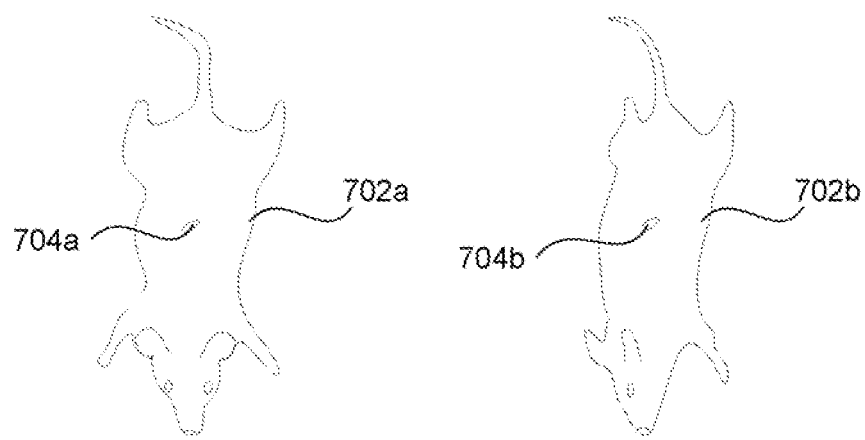
FIGS. 5E and 5F represent reconstruction results for one point-like light source within a phantom mouse (e.g., plastic mouse having an embedded fiber optic).
Figure 5F:
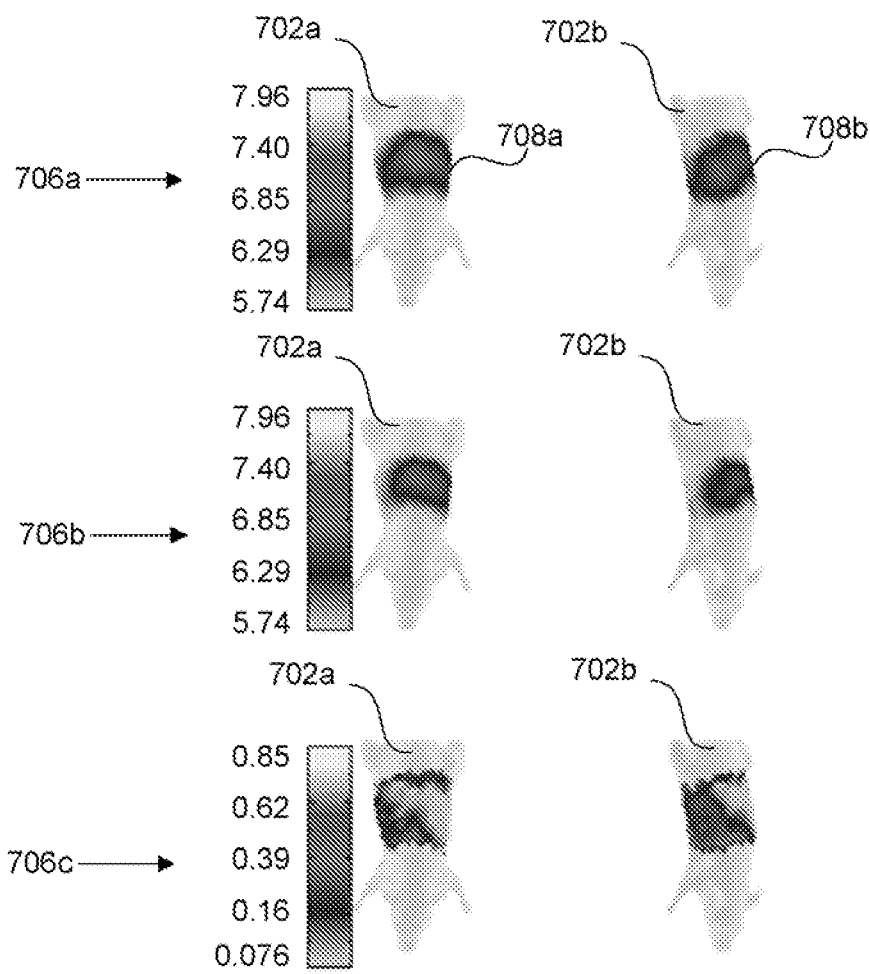

FIGS. 5E and 5F represent reconstruction results for one point-like light source within a phantom mouse (e.g., rubber mouse having an embedded fiber optic). FIG. 5E illustrates the reconstructed source distribution within phantom mouse 702a and 702b at two different angles. The surface shown represents the contour of the isosurface at half the maximum source strength. FIG. 5F shows images of the photon density (e.g., 708a and 708b) directly beneath the surface of the phantom mouse 702. The first row 706a is the logarithm of the measured photon density. The second row 706b is the logarithm of the simulated photon density, calculated from the reconstructed source distribution. The third row 706c is the difference of the first and second rows.

Although process flows 500, 510, 520 and 540 have been described with many simplifications to expedite processing, the present invention is not limited by these simplified computational methods. For example, the Green's Function may be calculated without many of the simplifications described above, even at the cost of increased computational requirements. In addition, while process flows 500, 510, 520 and 540 describe a specific method of obtaining measurements of light emission from the sample based on the system illustrated in FIGS. 1-2E, 3D reconstruction techniques of the present invention are not limited to how the 2D light emission data is obtained or to the use of any particular apparatus. Indeed, other imaging apparatus other than that described above with respect to FIGS. 1-2E may be used, such as an imaging apparatus described in commonly owned U.S. Pat. No. 7,113,217, which was previously incorporated by reference. In addition, 2D light emission data may be obtained from an independent source and stored as data within computer 28, and not necessarily produced as the result of imaging via a complementary or local imaging system.

Further, although the present invention has been described so far with respect to a bioluminescent source, the present invention may be used to obtain 3D reconstructions of any type of light sources, including one or more fluorescent sources. For a fluorescent source, the relationship between the surface elements and the volume elements may be altered (544). For example, a Green's function in the linear system may be multiplied by a second Green's function that describes the transport of the excitation light from the sample surface to the volume elements. In a specific approximation, the Green's function in the linear system (4) may be modified to be the product of two Green's functions:

$$G_{ij} = G_i^E G_{ij}^F \quad (15)$$

The first Green's function, $G_i^E$, describes the transport of excitation light from the excitation source at the surface of the sample to the $i^{th}$ volume element. The second Green's function, $G_{ij}^F$, describes the transport of the fluorescent light from the $i^{th}$ volume element to the $j^{th}$ surface element. Both Green's functions can be determined from analytical expressions, such as the simplified approximation described above in the case of a homogeneous medium, or from look-up tables in the case of an inhomogeneous medium. The excitation and fluorescent light are typically at different wavelengths, and thus the fluorescence does not stimulate additional fluorescence. The system of linear equations (4) is still valid, and process flow 540 can be used as outlined above to determine the fluorescent light source distribution.

The present invention is also well suited to handle noise in the input images. Any practical imaging system will have a limited dynamic range and be subject to noise sources. This may compromise the fidelity of the images used as input data in the reconstruction, and consequently may degrade the quality of the 3D representation. To this end, the present invention may also include techniques designed to improve its performance when the input images are noisy and/or have a limited dynamic range.

A limited dynamic range is particularly evident when imaging bioluminescence from sources imbedded in tissue, because the light emission intensity typically varies over many orders of magnitude across the sample surface. If the imaging camera imposes a limited dynamic range and a region of highest intensity is set to the camera's upper limit, then there will probably be regions in the image where the emission intensity falls below the bottom of the dynamic range. These regions of the image will be received as noise; and correspond to a 'noise floor'.

The reconstruction techniques provided herein map images of surface light emission onto the three-dimensional sample to determine the value of the photon density underneath the surface. With noise in the images, the reconstruction techniques map only those regions of the images that are above the noise floor. This can be done by defining a threshold for each image that is a fraction of the peak intensity. In one embodiment, the threshold is related to the peak intensity and dynamic range of the camera. In a specific embodiment, the threshold may be larger than the number represented by dividing the peak intensity by the dynamic range. For example, if the dynamic range of the camera is 1000 and the peak intensity in the image is $I_P$, than a suitable value for the threshold may be $I_P/500$. Only the regions of the image that are above the threshold are mapped onto the sample; and those regions below the threshold are not used. As a result, there will be regions of the sample surface that are empty after mapping is completed, that is, that have no photon density values associated with the surface mesh. Typically, these will tend to be the parts of the surface that are the farthest away from the bioluminescent source.

Process flow 540 solves the following optimization problem: maximize the total source strength subject to the constraint that the calculated photon density is less than the measured photon density everywhere on the surface. However, process flow 540 may also account for empty parts of the surface. This is because when the photon density is unknown, the constraints on the source strength are removed for those volume elements near the empty regions. Thus, there may be insufficient information to determine the source strength in those volume elements. The modification of process flow 540 consists of eliminating volume elements in the volume grid that are insufficiently constrained by the existing photon density information. This is achieved by comparing the contribution of a volume element to the photon density in the empty and non-empty surface regions. For example, if P and Q represent the sets of surface elements that consist of the empty and non-empty regions, respectively, then the criteria for removing the $i^{th}$ volume element from the volume grid is:

$$\sum_{j \in Q} G_{ij} < \kappa \sum_{j \in P} G_{ij} \quad (16)$$

The constant $\kappa$ may have a value in the range of 1-10. The criteria (16) is applied to each volume element during the formation of the initial volume grid (542) and at each iteration, if used.

In addition to having a limited dynamic range, realistic images may contain noise. One minimum noise contribution may be represented by the shot (Poisson) noise associated with the sampling of discrete numbers of photons in each image pixel. When shot noise dominates, the signal-to-noise ratio in the image varies with the square root of intensity. This suggests that the regions of highest intensity, or equivalently those regions of the surface having the highest photon density, should have the relatively smallest amount of noise. To account for this noise, the assessment for solution quality may altered (552). For example, expression (13) may be modified to account for noise. More specifically, each term in the sum may be weighted by a factor of the photon density $\rho_i$ to become:

$$\chi^2 = \sum_j \frac{1}{\rho_j} \left[ \rho_j - \sum_i G_{ij} S_i \right]^2 \quad (17)$$

Figure 6:
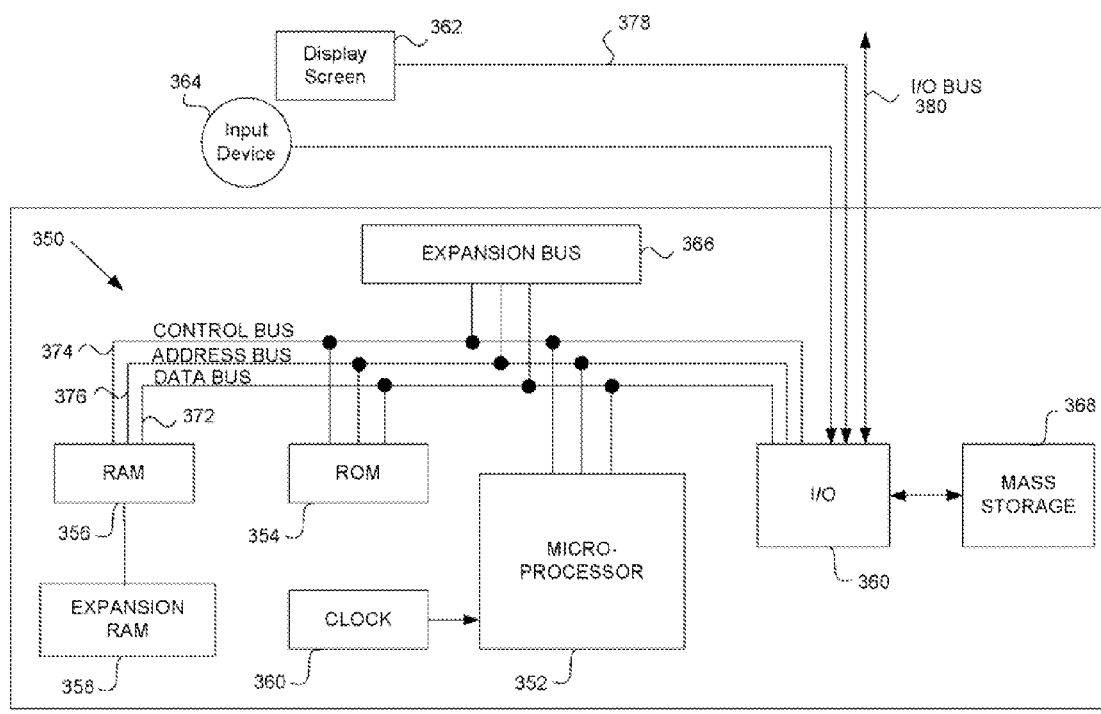
FIG. 6 illustrates an exemplary computer system in accordance with one embodiment of the present invention.

The reconstruction techniques of the present invention will typically be implemented by a suitable processor or computer-based apparatus. Referring to FIG. 6, an exemplary computer system 350 includes a central processing unit (CPU) 352, read only memory (ROM) 354, random access memory (RAM) 356, expansion RAM 358, input/output (I/O) circuitry 360, display assembly 362, input device 364, and expansion bus 366. Computer system 350 may also optionally include a mass storage unit 368 such as a disk drive unit or nonvolatile memory such as flash memory and a real-time clock 360.

Regardless of computer system 350 configuration, it may employ one or more memories or memory modules configured to store program instructions for obtaining a three-dimensional representation of a light source located inside a sample and other functions of the present invention described herein. Such memory or memories may also be configured to store data structures, imaging data, or other specific non-program information described herein.

Because such information and program instructions may be employed to implement the systems/methods described herein, the present invention relates to machine-readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

It should be borne in mind that although computer system 350 is discussed in some detail herein to facilitate discussion, the invention may be practiced using a variety of suitable computer-implemented techniques. In general, any suitable computer system may be employed for obtaining a three-dimensional representation of a light source located inside a sample. Further, the inventive reconstruction techniques disclosed herein may be implemented via a computer network, such as a local area network (LAN), wide area network (WAN) or a global computer network such as the Internet. In the latter cases, the reconstruction techniques may be implemented at least in part as downloadable computer software and data (e.g., applets such as JAVA™ applets from Sun Microsystems Inc.). The downloadable computer software and data may be kept on one or more servers on the network, accessible by any client computer or terminal capable and authorized for such access. Network computing techniques and implementations are well known in the art and are not discussed in great detail here for brevity's sake.

While this invention has been described in terms of several preferred embodiments, there are alterations, permutations, and equivalents which fall within the scope of this invention which have been omitted for brevity's sake. For example, images may be acquired and analyzed at one or more different wavelengths. It is therefore intended that the scope of the invention should be determined with reference to the appended claims.

What is claimed is:

1. A method for modeling an internal light source within an imaging subject, comprising:
   capturing surface light image data by measuring light that is generated by the light source within the imaging subject and is emitted from at least a portion of a surface of the imaging subject, wherein the light source comprises tissue that at least one of luminesces and fluoresces to generate the light;
   converting the surface light image data into a plurality of values of photon density, wherein each value of photon density is associated with a different surface element from among a set of surface elements that model the at least a portion of the surface and one or more volume elements representing a region of the subject; and
   using a processor to determine a three-dimensional representation of the internal light source based on the photon density values.

2. The method of claim 1, wherein the three-dimensional representation of the internal light source is approximated by a set of point light sources.

3. The method of claim 1, further comprising the step of: defining a cost function and a set of constraints to determine the three-dimensional representation of the internal light source.

4. The method of claim 3, wherein the cost function comprises a weighting factor that is varied to determine the three-dimensional representation of the internal light source.

5. The method of claim 1, further comprising applying a noise threshold to the surface light image data.

6. The method of claim 1, further comprising placing the imaging subject on a stage within an imaging chamber coupled to a camera, wherein the camera is configured to measure the light emitted from the at least a portion of the surface of the imaging subject when the imaging subject is positioned on the stage.

7. The method of claim 6, further comprising:
   moving the stage to multiple positions in the imaging chamber, wherein each of the multiple positions corresponds to a different angle relative to a fixed datum associated with the camera; and
   for each of the multiple positions, measuring the light emitted from the at least a portion of the surface of the imaging subject using the camera.

8. A system adapted to model an internal light source comprising tissue that at least one of luminesces and fluoresces within an imaging subject, the system comprising:
   an imaging chamber comprising a set of walls enclosing an interior cavity;
   a camera adapted to measure light from the imaging subject while the imaging subject is located within the imaging chamber; and
   a processing system configured to:
      obtain surface light image data by using the camera to measure light that is generated by the light source within the imaging subject and emitted from at least a portion of a surface of the imaging subject;
      obtain a three-dimensional representation of the at least a portion of the surface, wherein the three-dimensional representation comprises a set of surface elements that model the surface;
      map the surface light image data to the three-dimensional representation of the at least a portion of the surface by associating a photon density value with each of the surface elements; and
   determine a three-dimensional representation of the internal light source based on the mapped surface light image data.

9. The system of claim 8, further comprising a stage adapted to support the imaging subject, wherein the stage is moveable to one of a plurality of positions in the interior cavity.

10. The system of claim 8, further comprising a structured light projector.

11. The system of claim 8, wherein the imaging chamber is substantially light tight.

12. The method of claim 3, further comprising using the processor to determine the three-dimensional representation of the internal light source by optimizing the cost function subject to the set of constraints.

13. The method of claim 12, wherein the cost function comprises a set of point source strengths that represent the internal light source, and wherein each point source strength corresponds to a photon emission rate.

14. The method of claim 13, wherein the set of constraints comprises a condition that a sum of the point source strengths is positive definite.

15. The method of claim 3, wherein the set of constraints comprises a condition that, for each surface element, a set of all contributions to photon density from the point source strengths is less than the value of photon density derived from the surface light image data and associated with the element.

16. The method of claim 1, further comprising using the processor to:
    determine a first set of point source strengths that represent the internal light source based on a total number of volume elements representing the internal region of the imaging subject;
    adjust the total number of volume elements; and
    determine a second set of point source strengths the represent the internal light source based on the adjusted total number of volume elements.

17. The method of claim 16, further comprising using the processor to adjust the total number of volume elements by eliminating volume elements that correspond to source strengths of zero among the first set of point source strengths.

18. The method of claim 16, further comprising using the processor to adjust the total number of volume elements by subdividing volume elements that correspond to positive source strengths among the first set of point source strengths.

19. The system of claim 8, wherein the processing system is configured to determine the three-dimensional representation of the internal light source by optimizing a cost function subject to one or more constraints.

20. The system of claim 19, wherein the cost function comprises a set of point source strengths that represent the internal light source, and wherein each point source strength corresponds to a photon emission rate.

21. The system of claim 20, wherein the one or more constraints comprises a condition that a sum of the point source strengths is positive definite.

22. The system of claim 20, wherein the one or more constraints comprises a condition that, for each surface element, a set of all contributions to photon density from the point source strengths is less than the value of photon density associated with the element.

23. The system of claim 8, wherein the processing system is further configured to:
    determine a first set of point source strengths that represent the internal light source based on a total number of volume elements representing the internal region of the imaging subject;
    adjust the total number of volume elements; and
    determine a second set of point source strengths the represent the internal light source based on the adjusted total number of volume elements.

24. The system of claim 23, wherein the processing system is further configured to adjust the total number of volume elements by eliminating volume elements that correspond to source strengths of zero among the first set of point source strengths.

25. The system of claim 23, wherein the processing system is further configured to adjust the total number of volume elements by subdividing volume elements that correspond to positive source strengths among the first set of point source strengths.

* * * * *